US006413721B1

(12) United States Patent
Ogunremi et al.

(10) Patent No.: US 6,413,721 B1
(45) Date of Patent: Jul. 2, 2002

(54) METHODS OF ISOLATING COMMON AND SPECIFIC ANTIGENS FROM EXCRETORY-SECRETORY PRODUCTS OF PROTOSTRONGYLIDAE

(75) Inventors: Oladele Ogunremi; Alvin A. Gajadhar, both of Saskatoon (CA)

(73) Assignee: Her Majesty the Queen in Right of Canada, as represented by the "Canadian Food Inspection Agency", Sakatoon (CA)

( * ) Notice: Subject to any disclaimer, the term of this patent is extended or adjusted under 35 U.S.C. 154(b) by 0 days.

(21) Appl. No.: 09/359,082

(22) Filed: Jul. 22, 1999

Related U.S. Application Data

(60) Provisional application No. 60/094,064, filed on Jul. 24, 1998, and provisional application No. 60/094,117, filed on Jul. 24, 1998.

(51) Int. Cl.[7] ............................ G12Q 1/68; G01N 33/53; C12N 3/00; A61K 39/395; C07K 16/00

(52) U.S. Cl. .............................. 435/6; 435/7.1; 435/7.2; 435/7.22; 435/69.2; 435/69.4; 435/342; 435/965; 530/388.6; 424/178.1; 424/184.1; 424/265.1

(58) Field of Search ............................ 435/6, 7.1, 7.2, 435/7.22, 342, 965, 69.2–69.4; 530/388.6; 424/178.1, 184.1, 265.1

(56) References Cited

FOREIGN PATENT DOCUMENTS

| CA | WO0006721 | * | 2/2000 |
| WO | WO 94/26886 | | 11/1994 |

OTHER PUBLICATIONS

Saz Howard, 1981, Chapter 17, Medical Microbiology and infectious diseases, edited by Braude; W.B.Saunders Company, Philadelphia.*
Anderson, R.C., "Nematode Parasites of Vertebrates," C.A.B. International, Oxon, United Kingdom 161–166 (1992).
Anderson et al., Lungworms. In: Diseases and Parasites of White–Tailed Deer, W.R. Davidson, F.A. Hayes, V. F. Nettles, F. E. Kellog (eds.). Tall Timbers Research Station, Tallahassee, United States, 266–317.
Anderson et al., "The Penetration of *Pneumostrongylus Tenuis* Into the Tissues of White–Tailed Deer," Can. J. Zool. 45:285–289 (1967).
Behrend et al., "*Pneumostrongylus Tenuis* White–Tailed Deer in Maine,"*J. Wildl. Manage* 32(4):963–966 (12968).
Bienek et al., "Meningeal Worm Evokes a Heterogeneous Response in Elk," *J. of Wildl. Dis.* 34:334–341 (1998).

Dew et al., "Parasite–Specific Immunoglobulin in the Serum and Cerebrospinal Fluid of White–Tailed (*Odocoileus Virginianus*) and Goats *(Capra Hircus)* With Experimentally Induced Parelaphostrongylosis," *J. Zoo Wildl. Med.* 23(3):281–287 (1992).
Duffy et al., Serodiagnosis of *Parelaphostrongylus Tenuis* in White–Tailed Deer *Odocoileus Virginianus*. In Proceedings of the International Union of Games Biologist XXI Congress, I.D. Thompson (ed.) Halifax, Nova Scotia, Canada pp. 92–95 (1993).
Gajadhar et al., "Diagnosis of *Elaphostrongylus Cervi* Infection in New Zealand Red Deer (*Cervus Elaphus*) Quarantined in Canada, and Experimental Determination of a New Extended Prepatent Period," *Can. Vet. Journal* 35:433–437 (1994).
Gajadhar et al., "Susceptibility of Mule Deer (*Odocoileus Hemionus*) and Two Species of North American Molluscs to *Elaphostrongylus Cervi* (Nematoda: Metastrongyloidea), " *J. Parasitol.* 81(4):593–596 (1995).
Gamble et al., "Diagnosis of Swine Trichinosis by Enzyme–Linked Immunosorbent Assay (ELISA) Using an Excretory–Secretory Antigen," *Vet. Parasit.* 13:349–361 (1983).
Mustafa, et al., "Identification and Characterization of Filarial Excretory Secretory Antigens of Diagnostic Importance," *J. of Parasit. Diseases* 19:91–44(1995).
Neumann et al., "Antigens of Adults and Third–Stage Larvae of the Meningeal Worm, *Parelaphostrongylus Tenuis* (Nematoda, Metastrongyloidea), " *J. Vet. Diagn. Invest.* 6:222–229 (1994).
Ogunremi et al., "Serological Diagnosis of *Parelaphostrongylus Tenuis* Infection in White–Tailed Deer and Identification of a Potentially Unique Parasite Antigen," *J. of Parasitiology* 85(1):122–127 (1999).
Platt, T.R., "Evolution of Elaphostrongylinae (Nematoda: Metastrongylidae: Protostrongylidae) Parasites of Cervids (Mammalia)," Proceedings of Helminthological Society of Washington 51(2):196–204 (1984).
Pybus et al., "*Parelaphostrongylus Andersoni* (Nematoda: Protostrongylidae) and *P. Odocoilei* in Two Cervid Definitive Hosts," *J. Parasitol* 70(4):507–515 (1984).

(List continued on next page.)

*Primary Examiner*—Lynette R. F. Smith
*Assistant Examiner*—Padma Baskar
(74) *Attorney, Agent, or Firm*—Robins & Pasternak LLP

(57) ABSTRACT

Novel Protostrongylidea antigens and early and accurate diagnostic methods for Protostrongylidae infection are disclosed. Novel *P. tenuis*-specific antigens and methods of discriminating between *P. tenuis* infection and infection with other closely-related members of the Protostrongylidae family are provided. Novel *E. cervi*-specific antigens and methods of discriminating between *E. cervi* infection and infection with other closely-related members of the Protostrongylidae family are provided.

2 Claims, 11 Drawing Sheets

OTHER PUBLICATIONS

Rickard et al., "Experimentally Induced Meningeal Worm (*Parelaphostrongylus Tenuis*) Infection in the Llama (*Lama Glama*): Clinical Evaluation and Implications for Parasite Translocation," *J. Zoo Wildl. Med.* 25(3):390–402 (1994).

Samuel et al., "Elk as a Potential Host for Meningeal Worm: Implications for Translocation," *J. Wildl. Manage* 56(4):629–639 (1992).

Welch, et al., "Reliabilty of Fecal Examination for Detecting Infections of Meningeal Worm in Elk," *Wildl. Soc. Bull.* 19:326–331 (1991).

* cited by examiner

METHODS OF ISOLATING COMMON AND SPECIFIC ANTIGENS FROM EXCRETORY-SECRETORY PRODUCTS OF PROTOSTRONGYLIDAE

PRIORITY CLAIM

This invention claims priority under 35 U.S.C. § 119(e) to U.S. Provisional Application 60/094,064, filed Jul. 24, 1998 and U.S. Provisional Application 60/094,117 filed Jul. 24, 1998, both of which disclosures are incorporated by reference in their entireties herein.

BACKGROUND

Infection with meningeal and tissue worms (Nematoda: Protostrongylidae) can result in serious neurological disease or death in certain ungulate hosts. The Protostrongylidae family of nematodes includes a variety of infectious species, for example, *Parelaphostrongylus tenuis* (meningeal worm), *Parelaphostrongylus andersoni*, *Parelaphostrongylus odocoilei*, *Elaphostrongylus rangiferi* and *Elaphostrongylus cervi* (tissue worm) (see, e.g., Platt (1984) for a discussion of various protostrongylidae). The nematode *Parelaphostrongylus tenuis* (*P. tenuis*) is widespread throughout wild white-tailed deer hosts (WTD; *Odocoileus virginianus*) in the eastern half of North America. (Anderson et al. (1992), Anderson and Prestwood (1981), Anderson and Streveli (1967)). Although symptoms may be mild in infected WTD, *P. tenuis* infection can result in fatal neurological disease in various cervids and camelids as well as in other wild and domesticated ruminants (Anderson and Prestwood, (1981)).

Development of a reliable and sensitive method for diagnosing infection with various meningeal worms has proven difficult. Currently, diagnosis is performed using the Baermann technique or a modified Baermann technique (see, e.g., Gajadhar et al. (1994) *Can. Vet. J.* 35:433–437). In brief, this method involves detecting the presence of dorsal-spined, first-stage larvae (L1) in the feces of infected animals. However, there are several limitations to this technique. In particular, the method does not routinely allow detection of low level infection, although these animals may exhibit clinical signs and even die (Dew et al., 1992; Samuel et al., 1992). The reasons that infected animals may fail to shed detectable numbers of larvae has not been entirely elucidated. The parasite load may be low or larvae shed intermittently (Welch et al., 1991). Alternatively, animals infected with only one worm, or worms of the same gender, will not shed larvae.

The Baermann technique also fails to provide early detection of infection. Because the pre-patent period is long, between 82–137 days (Rickard et al., 1994), infection may not be diagnosed for many months and repeated testing is often required. Yet another drawback of the Baermann method is that is does not distinguish between various species of the protostrongylidae family. Many of the dorsal-spined larvae detected in feces are morphologically indistinguishable between species. (Pybus and Samuel, 1984; Lankester and Hauta, 1989; Lankester and Fong, 1989). Thus, available diagnostic techniques cannot routinely differentiate between infection with different nematodes.

Studies directed at identifying antibodies in the serum of infected animals have not resulted in reliable diagnostic methods. Although anti-*P. tenuis* antibodies have been detected in the serum of elk (wapiti; *Cervus elaphus canadensis*, Neumann et al., 1994; Bienek et al., 1998) and of goats (Dew et al., 1992), these antibodies are inconsistently detected in the serum of the definitive host, WTD (Dew et al., 1992; Duffy et al., 1993). Furthermore, even in those studies in which antibodies were detected, they were not measurable until at least 75 days post-exposure. (Duffy et al., supra). In addition, the serological cross-reactivity of anti-*P. tenuis* antibody against antigens of the other closely related nematodes has not been assessed.

Thus, there remains a need for early and accurate identification of parasitic nematode infections. In addition, there is a need for identification of antigens that specifically and uniquely identify parasites such as *P. tenuis* or *E. cervi*.

SUMMARY OF THE INVENTION

Described herein are novel common and specific Protostrongylidea antigens, polynucleotides encoding these antigens and antibodies which recognize these antigens. Early and accurate diagnostic methods for parasitic infection are disclosed.

Thus, in one aspect, the invention includes isolated immunogenic Protostrongylidae antigens, for example a *P. tenuis*-specific 20 kDa antigen, a *P. tenuis*-specific 37 kDa antigen, an *E. cervi*-specific 37 kDa antigen, a 52 kDa antigen and a *P. tenuis*-specific 75 kDa antigen, a common 105 kDa antigen or a common 158 kDa antigen, as determined by SDS-PAGE gel electrophoresis. Thus, antigens specific for *P. tenuis* or *E. cervi* are also provided. Exemplary *P. tenuis*-specific antigens include a *P. tenuis*-specific 20 kDa antigen, a *P. tenuis*-specific 37 kDa antigen and a *P. tenuis*-specific 75 kDa antigen, as determined by SDS-PAGE gel electrophoresis. Exemplary *E. cervi*-specific antigens include an *E. cervi*-specific 37 kDa antigen and an *E. cervi*-specific 52 kDa antigen, as determined by SDS-PAGE gel electrophoresis.

In another aspect, antibodies that specifically recognize a common Protostrongylidae antigen are provided. Antibodies that specifically recognize *P. tenuis*-specific or *E. cervi*-specific antigens are also described.

In another aspect, the invention provides polynucleotides encoding common, *P. tenuis*-specific or *E. cervi*-specific antigens.

Methods of diagnosing Protostrongylidae infection in a vertebrate subject by detecting the presence of at least one common Protostrongylidae antigen in a biological sample, for example a serum sample, obtained from the subject are also provided. In some embodiments, the presence of one common antigen is detected, while in other embodiments, multiple common antigens are detected. Methods of specifically diagnosing *P. tenuis* or *E. cervi* infection using at least one *P. tenuis*-specific or *E. cervi*-specific antigens are also provided. The common or specific antigens can be detected, for example, using antibodies, using nucleic acid probes or using PCR. In one embodiment, the common or specific antigens are detected by (a) reacting the biological sample with one or more isolated common or one or more specific antigens under conditions which allow anti-Protostrongylidae, *P. tenuis* or *E. cervi* antibodies, when present in the sample, to specifically bind with said common antigens; (b) removing unbound antibodies; (c) providing one or more moieties capable of associating with the bound antibodies; and (d) detecting the presence or absence of the one or more moieties. The one or more moieties may comprise a detectably labeled immunoglobulin antibody.

In another aspect, methods of detecting, in a biological sample, antibodies to parasites comprising (a) reacting the biological sample with an antigen preparation selected from the group consisting of an ES-L3 antigen preparation and an sL3 antigen preparation, under conditions which allow parasitic antibodies to bind to an antigen in the antigen preparations and form an antigen:antibody complex; and (b) detecting the presence or absence of said complex are provided. The parasites may be a member of the Protostrongylidae family or may specifically be P. tenuis or E. cervi.

Kits for use in the diagnostic methods described herein are also provided. The kits comprise, in a suitable packaging, one or more common or P. tenuis- or E. cervi-specific antigens immobilized on a solid support; and a reagent suitable for detecting, in a biological sample, the presence of antibodies to the one or more common or P. tenuis- or E. cervi-specific antigens.

In yet another aspect, the invention common antigens obtained by (a) providing a cDNA library which expresses protostrongylidae genes; (b) screening the expressed genes of the cDNA library with a source of anti-protostrongylidae antibodies to identify cDNA clones which express common antigens; and (c) transforming a host cell with the cDNA clones which express the common antigen. Also provided are P. tenuis-specific antigens obtained by (a) providing a cDNA library which expresses P. tenuis genes; (b) screening the expressed genes of the cDNA library with a source of anti-P. tenuis antibodies to identify cDNA clones which express P. tenuis-specific antigens; and (c) transforming a host cell with the cDNA clones which express the P. tenuis-specific antigen. Also provided are E. cervi-specific antigens obtained by (a) providing a cDNA library which expresses E. cervi genes; (b) screening the expressed genes of the cDNA library with a source of anti-E. cervi antibodies to identify cDNA clones which express E. cervi-specific antigens; and (c) transforming a host cell with the cDNA clones which express the E. cervi-specific antigen.

In another aspect, methods of isolating common or specific antigens are provided. In one embodiment, the antigens are isolated from excretory-secretory (ES) products, for example from the third-larval stage. Alternatively, antigens can be isolated directly from L3 or from adult organisms.

These and other embodiments of the subject invention will readily occur to those of skill in the art in light of the disclosure herein.

Serum samples from caribou with E. rangiferi (Er) or concurrent E. rangiferi and P. andersoni (Er & Pa) infections were compared with serum from P. tenuis-infected white-tailed deer (Pt) for recognition of somatic P. tenuis L3 antigens by immunoblotting. WTD anti-P. tenuis serum uniquely recognized the 37 kDa antigen of P. tenuis L3.

Figure 4:
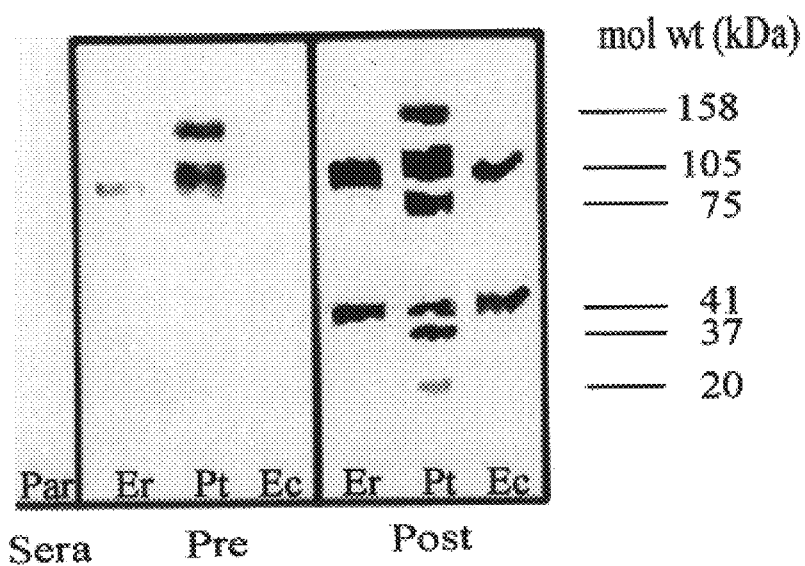
Figure 5A:
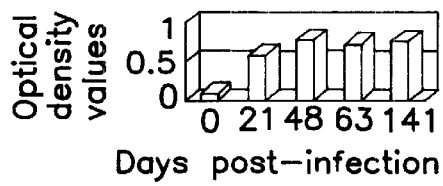
Figure 5B:
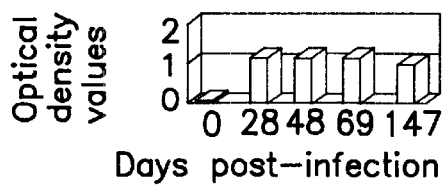
Figure 5C:
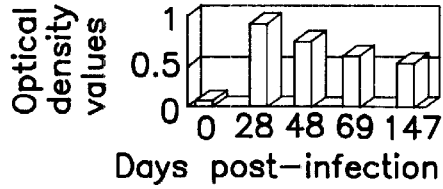
Figure 5D:
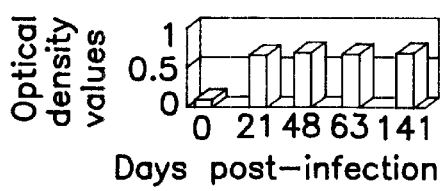
Figure 5E:
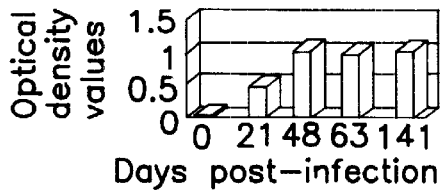
Figure 5F:
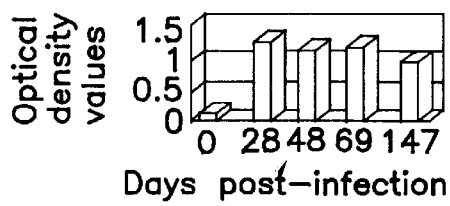
Figure 5G:
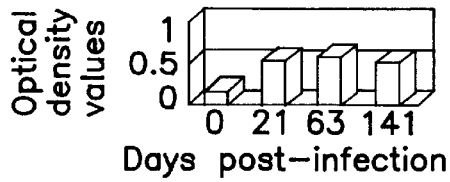
Figure 5H:
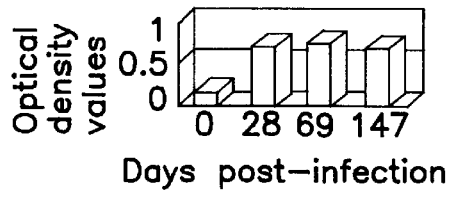
Figure 5I:
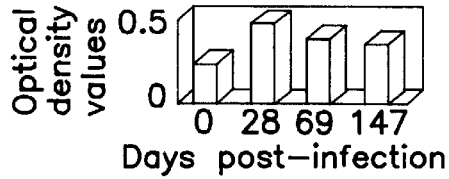
Figure 5J:
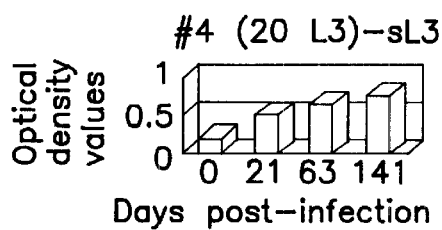
Figure 5K:
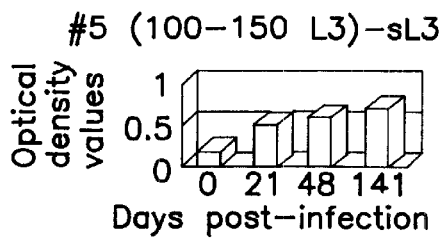
Figure 5L:
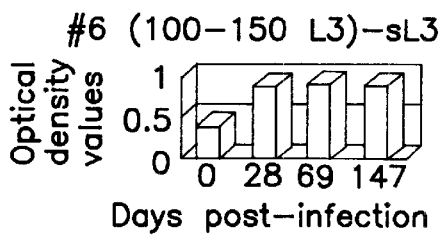
Figure 5M:
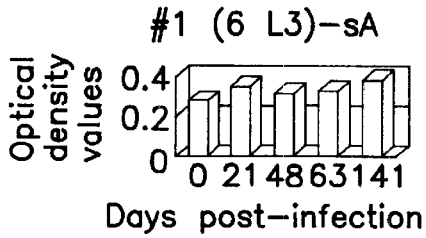
Figure 5N:
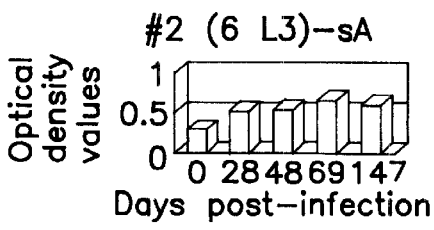
Figure 5O:
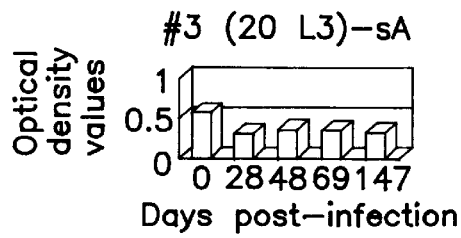
Figure 5P:
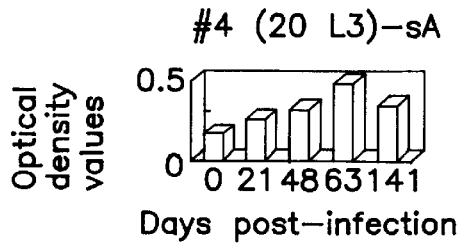
Figure 5Q:
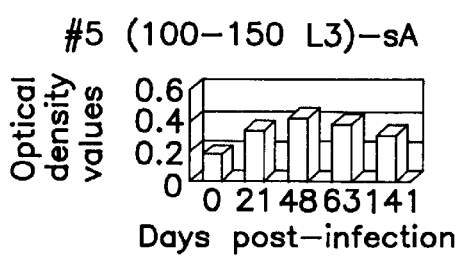
Figure 5R:
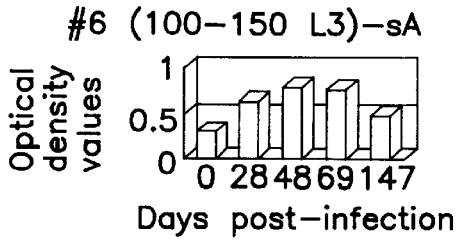

FIG. 4 shows unique recognition of adult P. tenuis antigens by White-tailed deer serum before (pre) and after (post) infection with parasite. Serum obtained from P. tenuis-infected white-tailed deer (post) reacted with a 37 kDa antigen, a 20 kDa antigen, and a 75 kDa antigen present in adult P. tenuis (Pt), but did not react with any antigen of similar size in the other parasites (Par), e.g., adult E. rangiferi (Er) or E. cervi (Ec). Pre-infection serum (Pre) did not recognize the specific antigens in P. tenuis, E. rangiferi or E. cervi.

FIG. 5, panels A–R, are graphs depicting optical density values of indirect ELISAs using excretory-secretory products of third-stage larvae (ES-L3), somatic antigens of third-stage larvae (L3), and somatic antigens (sA) of adult P. tenuis reacted with anti-P. tenuis antibodies from adult WTD. The heading on each panel refers to the animal ("#") and, in parentheses, the number and stage of larvae used to infect the animal. The left column of panels (A–F) shows ES-L3 antigens, the middle column (panels G–L) shows L3 antigens and the right hand column of panels (M–R) shows sA antigens The x-axis of each graph shows the days, post-infection, that the serum samples were taken from the infected animals. Antibodies against ES-L3 and sL3 increased quickly following infection and remained high.

Figure 6:
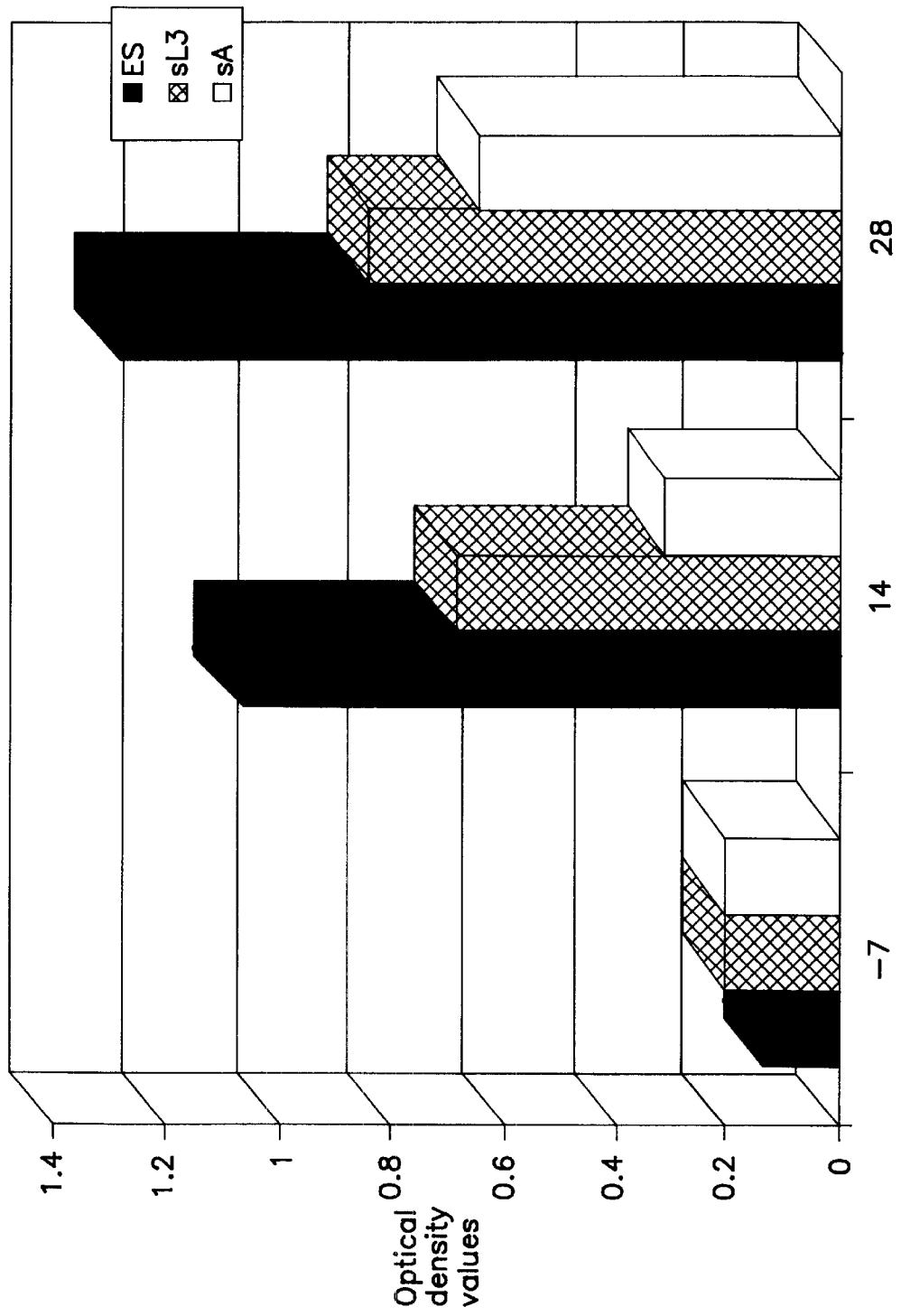

FIG. 6 depicts early detection of antibody to P. tenuis antigens using an indirect ELISA.

Figure 7:
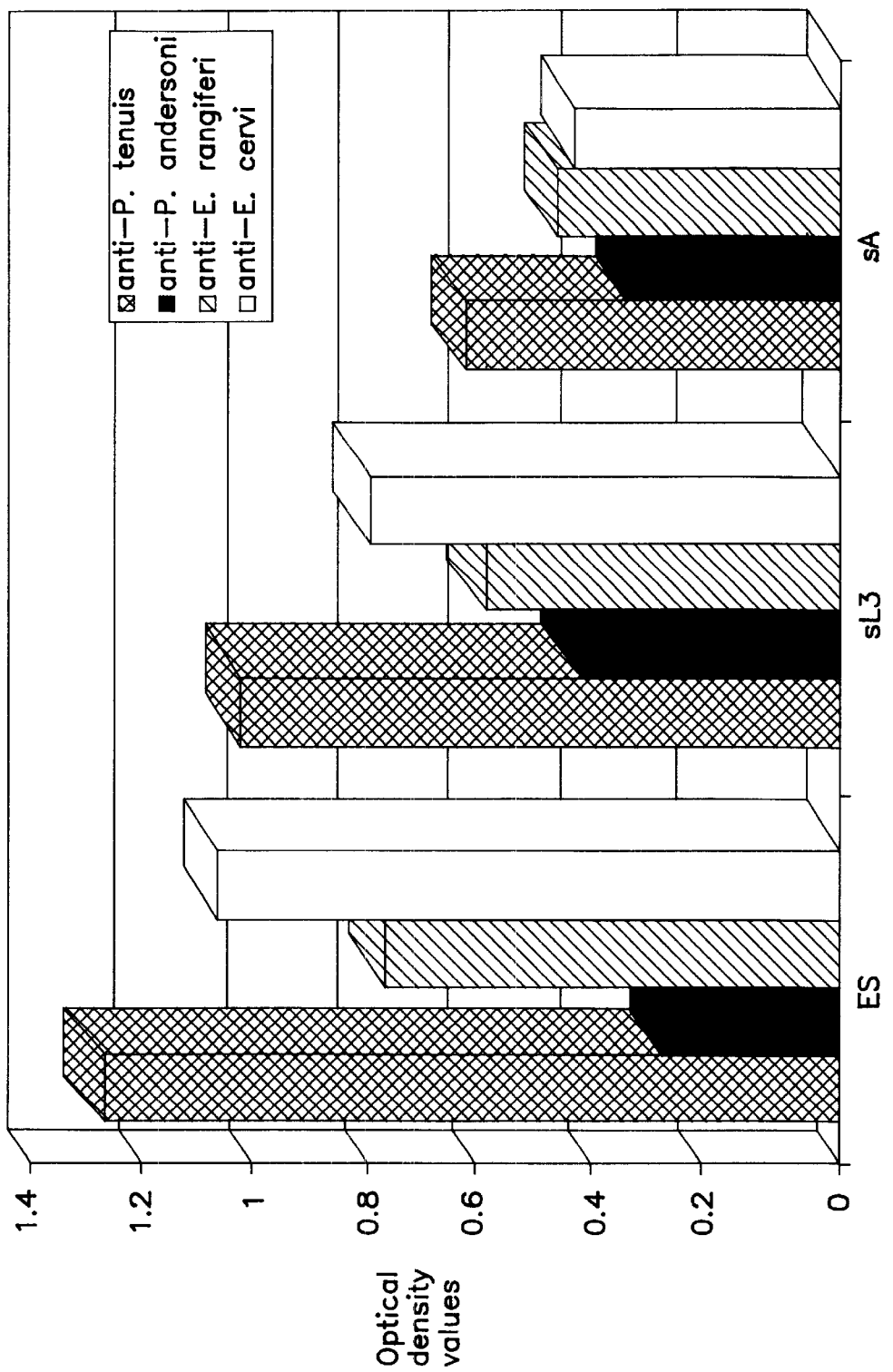

FIG. 7 depicts a comparison of antibodies obtained from P. tenuis, P. andersoni, E. rangiferi and E. cervi using an indirect ELISA.

Figure 8A:
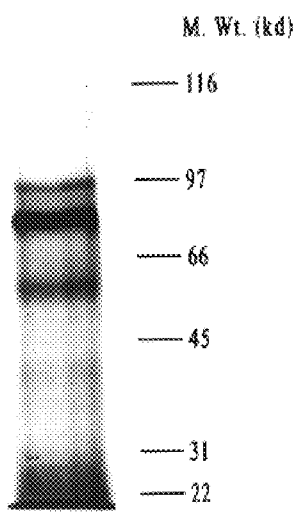
Figure 8B:
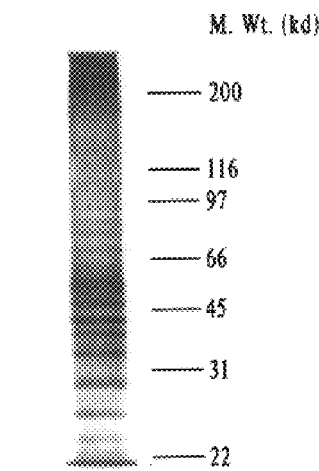
Figure 8C:
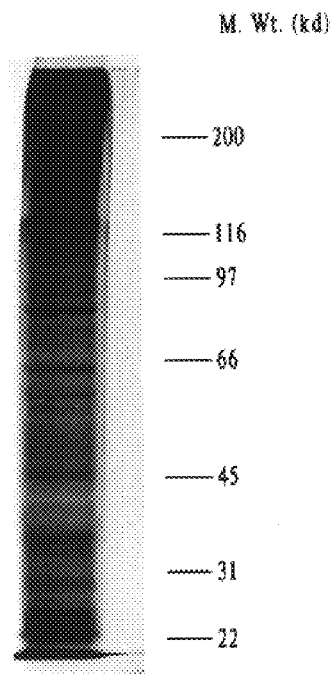

FIG. 8, panels A–C, are reproductions of photographs of an SDS-PAGE gel immunoblot of P. tenuis antigens obtained from ES-L3 (panel A), sL3 (panel B) or sA (panel C).

Figure 9:
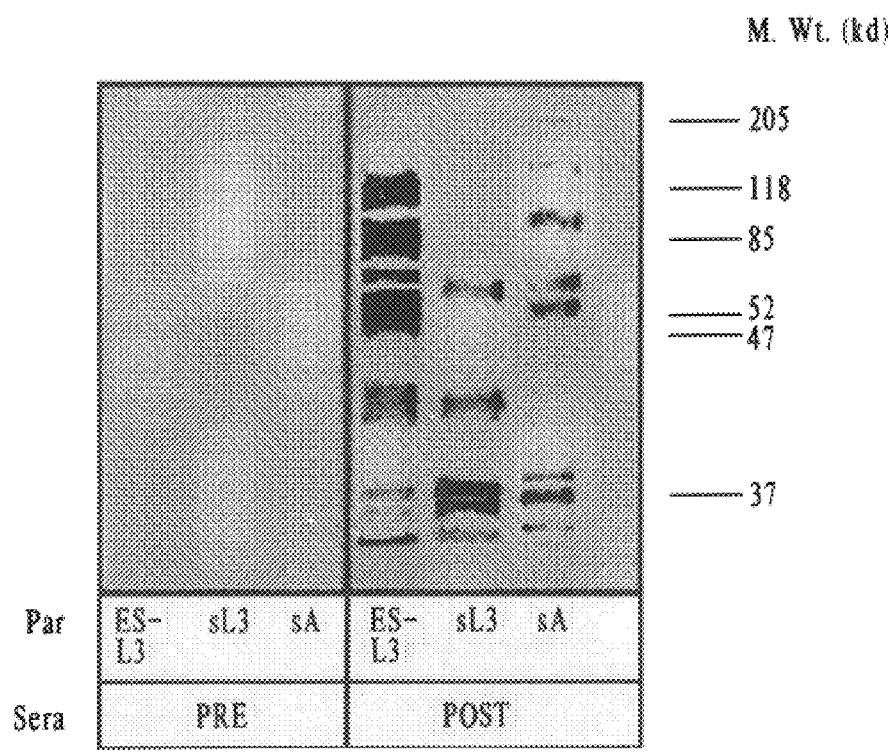

FIG. 9 depicts immunoblot analysis of P. tenuis antigens using serum obtained from an infected white-tailed deer.

Figure 10:
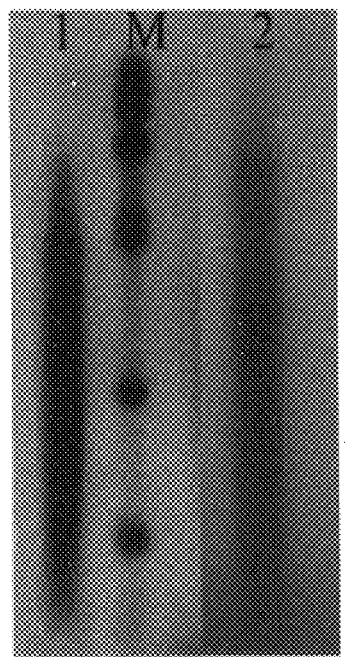

FIG. 10 is an autoradiograph depicting cDNA synthesized from P. tenuis total RNA.

Figure 11:
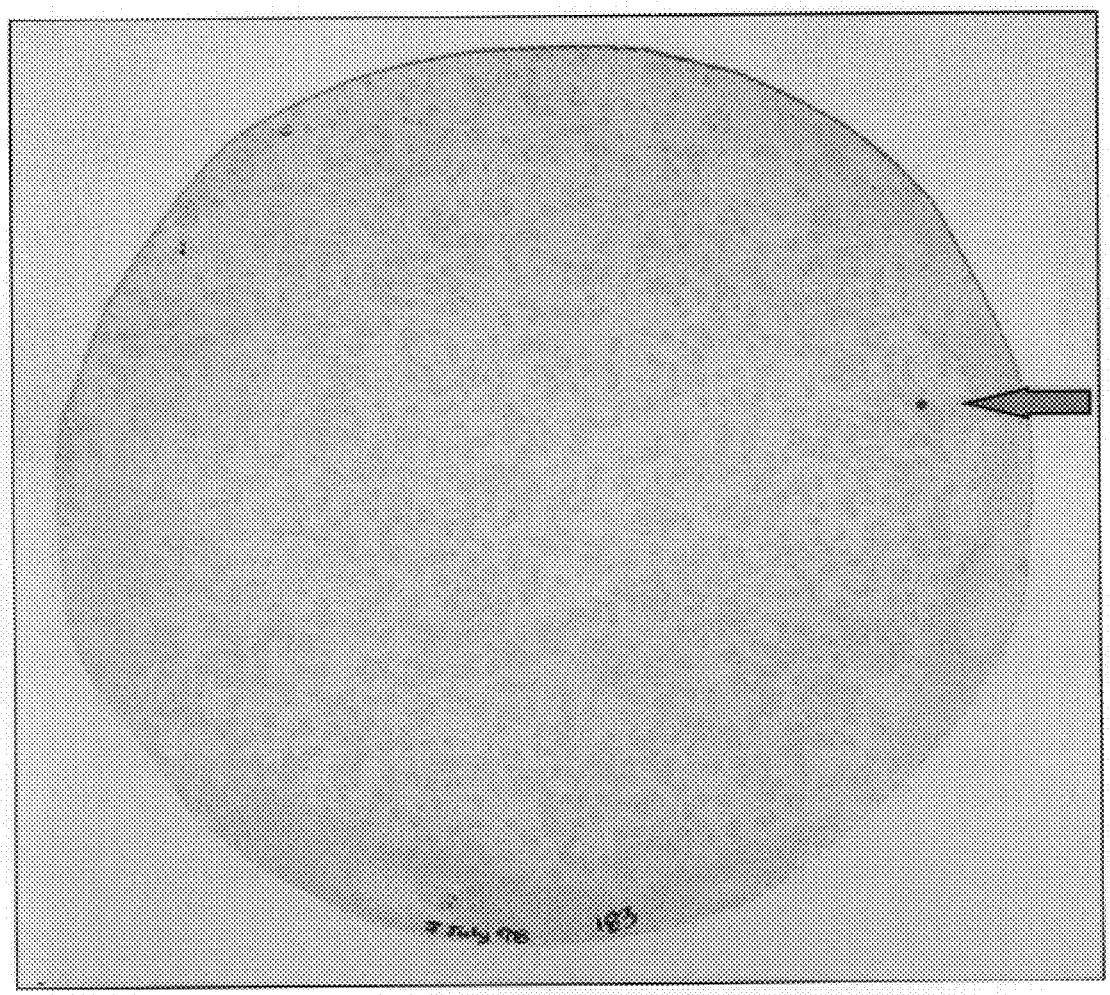

FIG. 11 depicts P. tenuis antigen-producing clones. E. coli XLI was infected with 6×10³ P. tenuis cDNA-UNIZAP phages of the amplified library, and grown on an NZY plate. Plaques produced by the lysis of bacteria were transferred to nitrocellulose and the presence of putative P. tenuis antigens identified with the antiserum. One plaque (arrow) produced antigen that reacted with anti-P. tenuis antiserunm.

Figure 12:
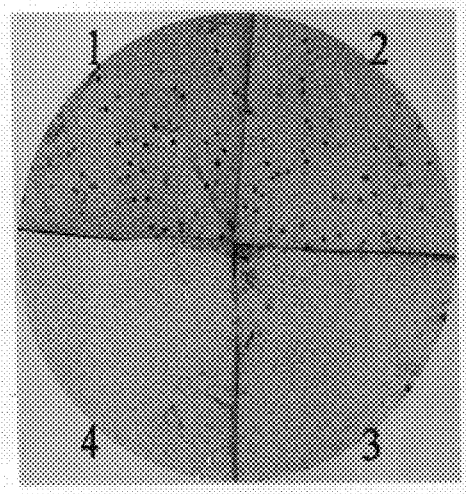

FIG. 12 is a reproduction of a photograph of a nitrocellulose membrane containing P. tenuis cDNA clones identified from primary screening with mouse anti-P. tenuis antiserum were re-screened with other sera/antisera (2. WTD anti-P. tenuis, 3. WTD normal serum, 4. Elk anti-Dictyocaulus) to assess cross-reactivity or uniqueness of clones.

Figure 13:
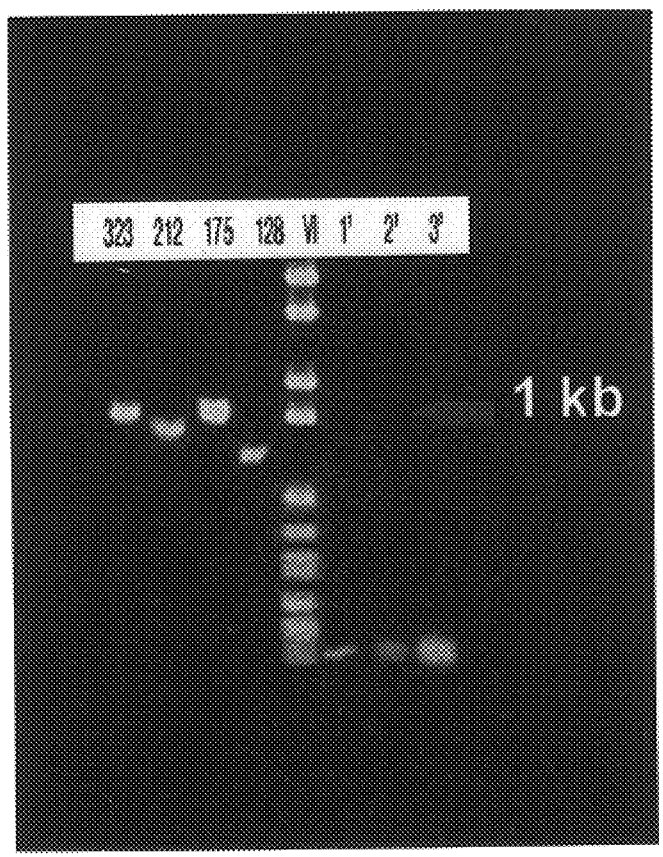

FIG. 13 depicts sizes of various cloned P. tenuis genes encoding antigens. The four right-most lanes show individual clones, labeled by clone number. The fifth lane from the right, labeled V1, show the molecular weight marker. The three left-most lanes, labeled 1', 2' and 3', are clones without inserts (controls).

Figure 14:
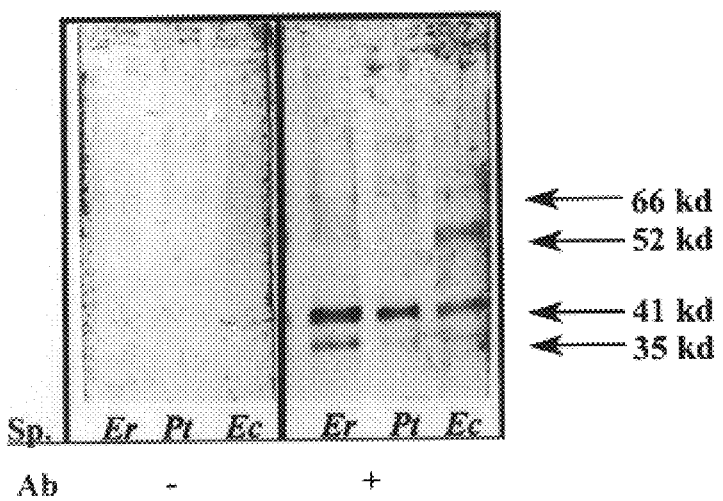

FIG. 14 shows unique recognition of adult E. cervi (Ec) antigens in red deer serum before ("−") and after ("+")

infection with parasite. Serum obtained from *E. cervi*-infected red deer ("+") reacted with a 52 kDa present in *E. cervi* (Ec), but did not react with any antigen of similar size in the other parasites, e.g., adult *E. rangiferi* (Er) or *P. tenuis* (Pt). Pre-infection serum ("−") did not recognize the specific antigens in *P. tenuis, E. rangiferi* or *E. cervi*.

DETAILED DESCRIPTION OF THE INVENTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a *P. tenuis* antigen" includes a mixture of two or more *P. tenuis* antigens, and the like.

The term "polypeptide" or "protein" when used with reference to an antigen, such as a *P. tenuis*-specific or *E. cervi*-specific antigen described herein, refers to polypeptides, whether native, recombinant or synthetic, which are derived from any of the various parasitic strains, particularly from the family Protostrongylidae. In the case of antigens specific for *P. tenuis*, the polypeptide will be derived from a *P. tenuis* strain. In the case of antigens specific for *E. cervi*, the polypeptide will be derived from a *E. cervi* strain. The polypeptide need not include the full-length amino acid sequence of the reference molecule but can include only so much of the molecule as necessary in order for the polypeptide to react with the appropriate antibodies. Thus, only one or few epitopes of the reference molecule need be present. Furthermore, the polypeptide may comprise a fusion protein between the full-length reference molecule or a fragment of the reference molecule, and another protein that does not disrupt the immunogenicity of the antigenic polypeptide. It is readily apparent that the polypeptide may therefore comprise the full-length sequence, fragments, truncated and partial sequences, as well as analogs and precursor forms of the reference molecule. The term also intends deletions, additions and substitutions to the reference sequence, so long as the polypeptide retains the ability to react with the anti-parasite antibodies.

In this regard, particularly preferred substitutions will generally be conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Proteins having substantially the same amino acid sequence as the reference molecule, but possessing minor amino acid substitutions that do not substantially affect the antibody binding capabilities of the protein, are therefore within the definition of the reference polypeptide.

An "antigen" refers to any molecule or compound which elicits a humoral or cell-mediated immune response. As used herein, a "*P. tenuis*-specific antigen" is any antigen (e.g., polypeptide) derived from *P. tenuis* which reacts predominantly with antibodies against *P. tenuis* but not with antibodies against other closely related parasitic nematodes of the family Protostrongylidae. Representative *P. tenuis*-specific antigens include, but are not limited to, a 20 kDa antigen, a 37 kDa antigen (referred to as "a 37 kDa *P. tenuis*-specific antigen" to distinguish from the *E. cervi*-specific antigen having the same apparent molecular weight) and a 75 kDa antigen. Molecular weights of the antigens are determined using standard gel electrophoresis protocols, for example as described below in the Examples, 10% SDS page gels under reducing conditions. Similarly, an "*E. cervi*-specific antigen" is any antigen that reacts predominantly with antibodies against *E. cervi*. Representative *E. cervi*-specific antigens include, but are not limited to, a 37 kDa antigen isolated from third-stage larvae (referred to as "a 37 kDa *E. cervi*-specific antigen" to distinguish from the *P. tenuis* specific antigen of the same apparent molecular weight) and a 52 kDa antigen. Antigens that react with various members of the Protostrongylidae family (e.g., *E. cervi, P. andersoni, E. rangiferi, P. tenuis*) are termed "common" antigens. Non-limiting examples of common antigens include a 105 kDa antigen and 158 kDa antigen.

By "epitope" is meant a site on an antigen to which specific B cells and/or T cells respond. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids and conformational epitopes of a given protein are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed directed serology. See, also, Geysen et al., *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody).

Antibodies that recognize the same epitope can be identified in a simple immunoassay showing the ability of one antibody to block the binding of another antibody to a target antigen. See, for example, "Epitope Mapping Protocols in Methods in Molecular Biology," vol. 66 (Glenn E. Morris, Ed., 1996) Humana Press, Totowa, N.J.

By "subunit antigen composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit antigen composition" is prepared from at least partially purified (preferably substantially purified) immunogenic polypeptides from the pathogen, or recombinant analogs thereof. A subunit antigen composition can comprise the subunit antigen or antigens of interest substantially free of other antigens or polypeptides from the pathogen.

A "purified" protein or polypeptide is a protein which is recombinantly or synthetically produced, or isolated from its natural host, such that the amount of protein present in a composition is substantially higher than that present in a crude preparation. In general, a purified protein will be at least about 50% homogeneous and more preferably at least about 80% to 90% homogeneous.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, acradimum esters, NADPH and $\alpha$-$\beta$-galactosidase.

The term "isolated" means separated from constituents, cellular and otherwise, with which the polynucleotide, peptide, polypeptide, protein, antibody or fragments thereof, are normally associated with in nature. As is apparent to those of skill in the art, a non-naturally occurring polynucleotide, polypeptide, protein, antibody, or fragments thereof, does not require isolation to distinguish it from its naturally occurring counterpart.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is composed of a specific sequence of four nucleotide bases: adenine (A); cytosine (C); guanine (G); thymine (T); and uracil (U) for thymine (T) when the polynucleotide is RNA. Thus, the term polynucleotide sequence is the alphabetical representation of a polynucleotide molecule. This alphabetical representation can be input into databases in a computer having a central processing unit and used for bioinformatics applications such as functional genomics and homology searching.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A transcription termination sequence will usually be located 3' to the coding sequence.

DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to the percent identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs such as ALIGN, Dayhoff, M. O. (1978) in *Atlas of Protein Sequence and Structure* 5:Suppl. 3, National biomedical Research Foundation, Washington, D.C. Preferably, default parameters are used for alignment. One alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization, supra.*

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

By "vertebrate subject" is meant any member of the subphylum chordata, particularly mammals, including, without limitation, cervids, ruminants, humans, and primates. For example, the term includes red deer, white tailed deer, elk, moose, caribou and the like. The term does not denote a particular age. Thus, both adult and newborn individuals are intended to be covered.

General Overview

The present invention provides, in one aspect, novel parasitic antigens (e.g.,antigens from nematodes of the family protostrongylid) and fragments thereof. These antigens are useful in methods of diagnosing protostrongylidae infection in general.

The invention also provides, in another aspect, antigens which specifically and uniquely recognize *Parelaphostrongylus tenuis* (*P. tenuis*) infection. These *P. tenuis*-specific antigens can be used to distinguish *P. tenuis* infection from infection with other parasitic members of the Protostrongylidae family, for example *E. cervi, E. rangiferi, P. ocoilei* and *P. andersoni*. Antigens which specifically and uniquely recognize *E. cervi* infection are also provided. These *E. cervi*-specific antigens can be used to distinguish *E. cervi* infection from infection with other parasitic members of the Protostrongylidae family, for example *P. tenuis, E. rangiferi, P. ocoilei* and *P. andersoni*. Antibodies to these antigens and genes (e.g., nucleic acids) encoding the *P. tenuis*- or *E. cervi*-specific antigens are also provided.

The antigens and fragments thereof, antibodies thereto, and genes coding thereof, are useful as diagnostic reagents to detect the presence of infection in a vertebrate subject, for example, by testing a biological sample (blood, feces, etc.) obtained from these animals for the presence of these molecules. The presence or absence of antigens can be detected by a variety of methods, including, for example, use of antibodies, gel electrophoresis, ELISA, PCR, nucleic acid hybridization, or the like. For example, antibodies can be detected by reacting the putative antibody-containing sample with a parasitic antigen identified herein under conditions suitable for forming an antigen:antibody complex. The presence of such a complex is indicative of infection. Similarly, nucleic acid probes or primers specific for the genes encoding the antigen(s) of interest can be isolated or synthesized and the sample reacted under conditions such that the probe specifically hybridizes to the target sequence (or amplifies a PCR product). Thus, the invention includes methods of specifically diagnosing *P. tenuis* or *E. cervi* infection, by detecting the presence of *P. tenuis*- or *E. cervi* specific antigens and antibodies as well as diagnosing protostrongylidae infection in general. Thus, specific or common antigens (i.e., antigens that react with various members of the Protostrongylidae family) can be used to diagnose parasitic infection. It is to be understood that such diagnostic assays can be conducted using one or more common antigens, one or more specific antigens, or, alternatively, may use a combination of common and specific antigens.

In yet another aspect, the genes encoding the antigens can be cloned and used to design probes to detect and isolate homologous genes in other bacterial strains. For example, fragments comprising at least about 8–100 nucleotides, more preferably at least about 10–50 nucleotides, and most preferably about 12–30 or more nucleotides, will find use in these embodiments.

Antigens

The antigens described herein and active fragments and analogs derived from the same, can be produced by a variety of methods. In one method, Protostrongylidae-common antigens and *P. tenuis*- or *E. cervi*-specific antigens can be isolated directly from the organisms (e.g., nematodes) which express the same. As described in detail below, the life cycle of these organisms are quite complex, involving larval and adult stages. Suitable sources (e.g., stages) for the novel antigens are disclosed herein and can be readily determined by one of skill in the art in view of the teachings of this specification. For example, in one aspect, antigens can be isolated from the excretory-secretory products of the third larval stage (ES-L3) or directly from L3 or adult organisms. Generally, antigens (both common and specific) can be isolated by first preparing a crude extract which lacks cellular components and several extraneous proteins. The desired antigens can then be further purified, i.e, by column chromatography, HPLC, immunoadsorbent techniques or other conventional methods well known in the art. The antigens may be tested for specificity, for example as described in the Examples, by determining whether they bind to antibodies present in the serum of infected subjects. Once isolated, the amino acid sequence of the antigens can be readily determined, for example by cleavage and identification of the amino acid residues.

Alternatively, the antigens can be recombinantly produced. These recombinant products can take the form of partial protein sequences, full-length sequences, precursor forms that include signal sequences, mature forms without signals, or even fusion proteins (e.g., with an appropriate leader for the recombinant host, or with another antigenic sequence for *P. tenuis* or another pathogen).

The antigen-encoding genes of the present invention can be isolated using standard techniques, well known in the art. For example, gene libraries can be constructed and the resulting clones used to transform an appropriate host cell. Colonies can be pooled and screened using polyclonal serum or monoclonal antibodies to the *P. tenuis* or *E. cervi* antigen in question. As described in the Examples, cDNA clones can be prepared from mRNA of the parasite and these clones used to produce polypeptides which can be screened for their reactivity with antibodies. Both common and *E. cervi-* or *P. tenuis-*specific clones can be identified this way. Antigen-encoding genes of between about 500 and about 1,500 base pairs in size have been identified (see, Example 3).

Alternatively, once the amino acid sequences are determined, oligonucleotide probes which contain the codons for a portion of the determined amino acid sequences can be prepared and used to screen genomic or cDNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning:* Vol. 1, supra; *Nucleic Acid Hybridization,* supra; *Oligonucleotide Synthesis,* supra; Sambrook et al., supra. Once a clone from the screened library has been identified by positive hybridization, it can be confirmed by restriction enzyme analysis and DNA sequencing that the particular library insert contains a *P. tenuis* gene or a homolog thereof. The genes can then be further isolated using standard techniques and, if desired, PCR approaches or restriction enzymes employed to delete portions of the full-length sequence. Similarly, genes can be isolated directly from bacteria using known techniques, such as phenol extraction and the sequence further manipulated to produce any desired alterations. See, e.g., Sambrook et al., supra, for a description of techniques used to obtain and isolate DNA.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gran-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp 19 (Saccharomyces) and bovine papilloma virus (mammalian cells). See, Sambrook et al., supra; *DNA Cloning,* supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If a signal sequence is included, it can either be the native, homologous sequence, or a heterologous sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the *P. tenuis* antigen in question. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning,* supra; *Nucleic Acid Hybridization,* supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK")

cells, as well as others. Similarly, bacterial hosts such as *E. coli, Bacillus subtilis,* and Streptococcus spp., will find use with the present expression constructs. Yeast hosts useful in the present invention include inter alia, *Saccharomyces cerevisiae, Candida albicans, Candida maltosa, Hansenula polymorpha, Kluyveromycesfragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda,* and *Trichoplusia ni.*

Other systems for expression of the desired antigens include insect and plant cells and vectors suitable for use in these cells. The systems most commonly used are derived from the baculovirus *Autographa californica* polyhedrosis virus (AcNPV). Generally, expression in insect cells is achieved by using a bacterial plasmid which contains a fragment of the baculovirus genome and an insertion site for the heterologous gene (e.g., encoding the epitope of interest). Sufficient wild-type bacoluvirus sequence is also included both that the plasmid vector (and transgene) homologous recombine into the baculovirus genome.

Promoters for use in the vectors are typically derived from structural genes, abundantly transcribed at late times in a viral infection cycle. Examples include sequences derived from the gene encoding the viral polyhedron protein, Friesen et al., (1986) "The Regulation of Baculovirus Gene Expression" in: *The Molecular Biology of Baculoviruses* (ed. Walter Doerfler); EP Publication Nos. 127,839 and 155,476; and the gene encoding the p10 protein Vlak et al., *J. Gen. Virol.* (1988) 69:765. The plasmid usually also contains the polyhedrin polyadenylation signal (Miller et al., *Ann. Rev. Microbiol.* (1988) 42:177) and a procaryotic ampicillin-resistance (amp) gene and origin of replication for selection and propagation in *E. coli.* DNA encoding suitable signal sequences can also be included and is generally derived from genes for secreted insect or baculovirus proteins, such as the baculovirus polyhedrin gene (Carbonell et al., *Gene* (1988) 73:409), as well as mammalian signal sequences such as those derived from genes encoding human α-interferon, Maeda et al., *Nature* (1985) 315:592; human gastrin-releasing peptide, Lebacq-Verheyden et al., *Molec. Cell. Biol.* (1988) 8:3129; human IL-2, Smith et al., *Proc. Natl. Acad. Sci. USA* (1985) 82:8404; mouse IL-3, (Miyajima et al., *Gene* (1987) 58:273; and human glucocerebrosidase, Martin et al., *DNA* (1988) 7:99.

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, N.Y., (1980), pp. 3–254, for solid phase peptide synthesis techniques; and M. Bodansky, *Principles of Peptide Synthesis,* Springer-Verlag, Berlin (1984) and E. Gross and J. Meienhofer, Eds., *The Peptides: Analysis, Synthesis, Biology, supra,* Vol. 1, for classical solution synthesis. Chemical synthesis of peptides may be preferable if a small fragment of the antigen in question is desired.

Antibodies

The protostrongylidae (e.g., *P. tenuis*-specific, *E. cervi*-specific and common antigens) of the present invention, or their fragments, can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348:363–370. If serum containing polyclonal antibodies is used, the polyclonal antibodies can be purified by immunoaffinity chromatography, using known procedures.

Monoclonal antibodies to the common and specific antigens and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the *P. tenuis* antigens or fragments thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies are also useful for diagnostic purposes.

Diagnostic Applications

As explained above, the antigens of the present invention may be used as diagnostics to detect the presence of reactive antibodies in a biological sample in order to determine the presence of infection. In particular, the antigens are used herein as diagnostics to detect the presence of reactive antibodies directed against the worms in a biological sample. Furthermore, antigens specific for certain nematodes (e.g., *P. tenuis* or *E. cervi*) can be used to differentiate between infection with members of the Protostrongylidae family. For example, the presence of antibodies reactive with the cross-reactive and/or the specific antigens can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more common or specific antigens) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2–13; Hashida et al., *J. Appl. Biochem.* (1984) 6:56–63; and Anjaneyulu and Staros, *International J. of Peptide and Protein Res.* (1987) 30:117–124.

After reacting the solid support with the solid phase component, any non-immobilized solid-phase components are removed from the support by washing, and the support-bound component is then contacted with a biological sample suspected of containing ligand moieties (e.g., antibodies against the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with an antigen of interest, for example an antigen common to various species of protostrongylidae or *P. tenuis-* or *E. cervi-*specific antigens). A biological sample containing or suspected of containing anti-antigen immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-Protostrongylid antigen ligands from a biological sample can be readily detected using a secondary binder comprising an antibody directed against the antibody ligands. For example, *E. cervi-* or *P. tenuis-*specific antigens can be used to detect antibodies in a sample with the aid of appropriate anti-species immunoglobulins (Ig). A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the *P. tenuis* antigens and antibodies specific for those antigens form complexes under precipitating conditions. In one particular embodiment, one or more common or specific antigens can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies directed against *P. tenuis, E. cervi* or other protostrongylidae species. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-*P. tenuis* (or anti-*E. cervi,* anti-common or mixtures thereof) antigen molecules is immobilized to a substrate. In this regard, an initial affinity purification of the sample can be carried out using immobilized antigens. The resultant sample preparation will thus only contain anti-*P. tenuis* (or anti-*E. cervi,* anti-common or mixtures thereof) moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled P. tenuis antigens (or anti-E. cervi antigens or anti-common antigens or mixtures thereof) are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the antigens, rather than the antigens themselves, can be used in the above-described assays in order to detect the presence of proteins in a given sample. These assays are performed essentially as described above and are well known to those of skill in the art.

In another embodiment, the presence of antigens (e.g., common or *E. cervi-* or *P. tenuis-*specific) can be detected at the nucleic acid level. In assaying for the presence of sequences encoding common or specific antigens, the nucleic acids of the biological sample are first extracted according to standard methods in the art. For instance, DNA can be isolated from a biological sample by ethanol precipitation and repeated phenol:chloroform extractions (see, e.g., Sambrook et al, supra). Alternatively, mRNA can be isolated using various lytic enzymes or chemical solutions according to procedures set forth in Sambrook et al. (1989), supra or extracted by nucleic acid-binding resins following the instructions provided by the manufacturer. The mRNA of the antigen of interest contained in the sample is then detected by hybridization (e.g., Northern blot analysis) and/or amplification procedures according to the methods known in the art and described herein.

Nucleic acid molecules having at least 10 nucleotides, preferably at least about 12 to at least about 25, and more preferably at least about 15 to at least about 20 nucleotides, and exhibiting sequence complementarity or homology to the common or specific antigens described herein find utility as hybridization probes. It is know that a "perfectly matched" probe is not needed for specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned antigen of interest is at least 80% identical to the homologous region of the target sequence, more preferably at least about 85% identical and even more preferably at least about 90% identical.

These probes can be used in radioassays (e.g., Southern and Northern blot analysis) to detect, prognose, diagnose or monitor various conditions and symptoms resulting from Protostrongylidae infection. The total size of the fragment, as well as the size of the complementary stretches, will depend on the intended use or application of the particular nucleic acid segment. Smaller fragments derived from the known sequences will generally find use in hybridization embodiments, wherein the length of the complementary region may be varied, such as between about 10 and about 100 nucleotides or even longer if preferred. Thus, probes having complementary sequences over stretches greater than about 10 nucleotides in length are generally preferred, so as to increase stability and selectivity of the hybrid, and thereby improve the specificity of the particular hybrid molecules obtained. Such fragments may be readily prepared, for example, directly synthesizing the fragment by chemical means, by application of nucleic acid reproduction technology, such as PCR technology with two priming oligonucleotides as described in U.S. Pat. No. 4,603,102, or by recombinant means. A preferred probe is about 25 to about 50, more preferably from about 50 to about 75 or even more preferably, about 50 to about 100 nucleotides in length.

In certain embodiments, it may be advantageous to employ nucleic acid sequences of the present invention in combination with appropriate means, such as a label, for detecting hybridization. A wide variety of appropriate indicator means are available, for example, fluorescent, radioactive, enzymatic or other ligands, such as biotin/avidin. In the case of enzyme tags, colorimetric indicator substrates are known to provide a detectable (by eye or by spectrophotometer) signal.

Hybridization reactions can be performed under conditions of different "stringency." Relevant parameters which affect stringency include temperature, ionic strength, time of incubation, the presence of additional solutes in the reaction mixture such as formamide, and the washing procedure. Higher stringency conditions are those conditions, such as high temperature and lower sodium ion concentration, which require higher minimum complementarity between hybridizing elements for a stable complex to form. Conditions that affect stringency are widely known, for example as described in Sambrook et al, supra.

Nucleotide probes may also be used as primers for the detection of genes in a sample. Amplification of target sequences can be performed by any method employing a primer-dependent polymerase capable of replicating a target sequence with reasonable fidelity, for example, natural or recombinant DNA polymerases such as T7 DNA polymerase, Klenow fragment of $E.\ coli$ DNA polymerase, and reverse transcriptase.

A preferred amplification method is PCR. General procedures for PCR are described, for example, in MacPherson et al., PCR: A Practical Approach, (IRL Press at Oxford University Press (1991)). PCR conditions for individual reactions can be empirically determined. A number of parameters influence the success of a PCR reaction. Among them are annealing temperature and time, extension time, $Mg^{2+}$ ATP concentration, pH, and the relative concentration of primers, templates and deoxyribonucleotides. See, e.g., U.S. Pat. Nos. 4,683,202; 4,683,195; 4,965,188 and 4,800,159 for a description of the PCR technique.

Alternatively, the probes can be attached to a solid support for use in high throughput screening assays using methods known in the art. U.S. Pat. Nos. 5,405,783; 5,412,087 and 5,445,934, for example, disclose the construction of high density oligonucleotide chips which can contain one or more of the sequences for common or specific antigens.

After amplification, the resulting DNA fragments can be detected by agarose gel electrophoresis followed by visualization with ethidium bromide staining and ultraviolet illumination. A specific amplification of common or specific antigens can be verified by demonstrating that the amplified DNA fragment has the predicted size, exhibits the predicted restriction digest pattern, and/or hybridizes to the correct cloned DNA sequence.

The above-described assay reagents, including, for example, the $P.\ tenuis$ antigens, or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Below are examples of specific embodiments for carrying out the present invention. The examples are offered for illustrative purposes only, and are not intended to limit the scope of the present invention in any way.

EXAMPLES

Example 1

Serological Diagnosis of $Parelaphostronglyus\ tenuis$ Infection and Identification of a Unique $P.\ tenius$ Antigen 1.A. Materials and Methods 1.A.1. Parasites and Sera Infective third-stage larvae (L3) of $P.\ tenuis$ were obtained by pepsin-HCl digestion of snails ($Triodopsis\ multilineata$) that had been exposed to the first-stage larvae (L1) of the parasite 8–16 weeks earlier. The L1 were extracted from the feces of $P.\ tenuis$-infected white tailed deer (WTD) from Grand Marais, Minn., USA (47°41'N, 90°35'W) (Forrester and Lankester, 1997). The L3 were used to infect WTD or to prepare somatic antigens. Adult $P.\ tenuis$ were obtained at postmortem from the meninges of the central nervous system of experimentally infected WTD (Slomke et al., 1995). Adult $Elaphostrongylus\ rangiferi$ were obtained from the chest and thigh muscles of four wild woodland caribou ($Rangifer\ tarandus\ caribou$) on the Avalon Peninsula, Newfoundland, Canada (46°47'N 54°10'W). One of the caribou also had adult $P.\ andersoni$ in its longissimus dorsi muscles. Serum samples were obtained from all caribou. Adult *E. cervi* were obtained from the loose connective tissue of the skeletal muscles in the axilla and inguinal regions of three red deer (*Cervus elaphus elaphus*) experimentally infected approximately six months prior with *E. cervi* L3 (Gajadhar et al., 1994). Serial serum samples were obtained from these red deer during the course of the infection. Serum samples were also obtained from an elk captured from Elk Island National Park, Alberta, Canada, observed to be shedding trematode eggs, and found at postmortem to have *Fascioloides magna*. All animals were euthanised with an overdose of xylazine hydrochloride (Rompun, Miles, Etobicoke, Ontario, Canada) followed by T61 (Hoechst, Montreal, Quebec, Canada).

1.A.2. Infection of White-Tailed Deer with *P. tenuis* and Blood Collection

WTD used in the study were acquired as week-old orphaned fawns and raised in captivity in Saskatchewan where *P. tenuis* does not occur (Anderson, 1992). The fawns were bottle-fed and maintained in an open paddock and before transportation to Thunder Bay, Ontario where they were held on clean concrete. All animals were 9.5 months old at the start of the experiment. For purposes of infection and blood collection, animals were anaesthetized with Rompun administered using a blowpipe and lightweight syringe. Two WTD were each orally inoculated with six *P. tenuis* larvae, two were given 20, and two were given between 100 and 150. Blood samples were collected from each animal 1 wk before inoculation and at different times until the end of the experiment at 147 day post-inoculation (dpi). All 6 WTD passed small numbers of Dictyocaulus larvae in their feces during the experiment but no adult specimens were recovered at necropsy. Two additional WTD were kept in Saskatchewan as uninfected, control animals. Maintenance and use of all experimental animals were according to the guidelines of the Canadian Council on Animal Care.

1.A.3. Somatic Parasite Antigens

Adult and L3 of *P. tenuis* and adults of *E. rangiferi* and *E. cervi* were washed in PBS, kept on ice and sonicated at 300 W, 1 min at a time for a total of 5 min or until no discernible worm fragments were microscopically visible. The parasite homogenate was centrifuged at 10,000 g for 5 min and the supernatant removed and stored at −20° C. until use. Protein concentrations of antigens were determined using the BCA kit (Pierce, Rockford, Ill., USA).

1.A.4. ELISA

Somatic antigens of *P. tenuis* L3 were diluted in PBS, pH 7.4, adsorbed to wells of microtitre plates (Immulon-4, Dynatech Lab, Chantilly, Va., USA) at 0.4 µg/well and incubated at 37° C. overnight. Unadsorbed proteins were washed off the wells with PBS containing 0.5% Tween 20 (PBST) using a plate washer. Predetermined optimal dilution (1:200) of WTD, caribou and elk sera were made in PBST, and applied at 50 µl/well after which the plates were incubated at 37° C. for 3 h. At the end of the incubation, plates were washed and alkaline phosphatase-labeled rabbit WTD IgG (Kirkegaard and Perry Laboratories, Gaithersburg, Md., USA), demonstrated to strongly cross-react with caribou and elk antibodies, was diluted in PBST (1:3,000) and applied at 50 µl/well. After a further 2 hour incubation at 37° C., wells of the plate were washed with PBST and phosphatase substrate (p-nitrophenyl phosphatase, Kirkegaard and Perry Laboratories, Gaithersburg, Md., USA) added. Color development was allowed to proceed for 1 hr in the dark, stopped by the addition of 5% ethylene diamine tetraacetic acid (EDTA) and measured at a wavelength of 405 nm with a spectrophotometer (Titertek Multiskan, Labsystems, Finland). ELISA results are shown as antibody titers or optical density (OD) values.

1.A.5. Immunoblotting

Somatic antigens of L3 or adult parasites were separated on a 10% SDS-Polyacrylamide gel at 160 V for 45 min, under reducing conditions. The separated proteins were transferred onto nitrocellulose membrane (BioRad, Hercules, Calif.) for immuno-staining. Membranes bearing the proteins were blocked with PBS containing 5% milk (milk-PBS). Deer or caribou sera were diluted 1 in 25 in 2.5% milk-PBS containing 0.1% Tween 20 (milk-PBST), applied to membranes and incubated overnight at room temperature. After incubation, the membranes were washed with PBST, following which alkaline phosphatase-labelled rabbit anti-deer IgG diluted 1 in 500 in milk-PBST was added. After 4 hours of incubation, the membrane was washed three times in PBST followed by a final wash in PBS. Color development reagent (BCIP/NBT phosphatase substrate, Kirkegaard and Perry Laboratories, Gaithersburg, Mass.) was added to the membrane and incubated in the dark. The development was stopped after 30 min by the addition of tap water to the membrane. Bands detected by immunoblotting were subjected to densitometric analysis by scanning (Sharp Scanner, Mahwah, N.J., USA) onto a computer equipped with the ImageMaster software (Pharmacia, Montreal, Canada).

1.A.6. Mathematical and Statistical Analyses

A regression analysis of optical density values against the reciprocal values of the dilutions were used to generate a straight line equation from which antibody titers were calculated (Lehtonen and Viljanen, 1982). Pre-infection antibody titers were arbitrarily set at 1 in 10. Correlations between dependent and independent variables were assessed by linear regression. Total antibody titers were calculated as the area under the curve generated by plotting the titers at the different bleeding times. Statistical significances were analyzed at the 95% confidence limits. All analyses were performed with the Prism computer program (GraphPad software, San Diego, Calif., USA).

1.B. Results

1.B.1. Anti-*P. tenuis* L3 Antibodies In Infected White-Tailed Deer

Figures 1A, 1B, 1C, 1D, 1E, 1F:
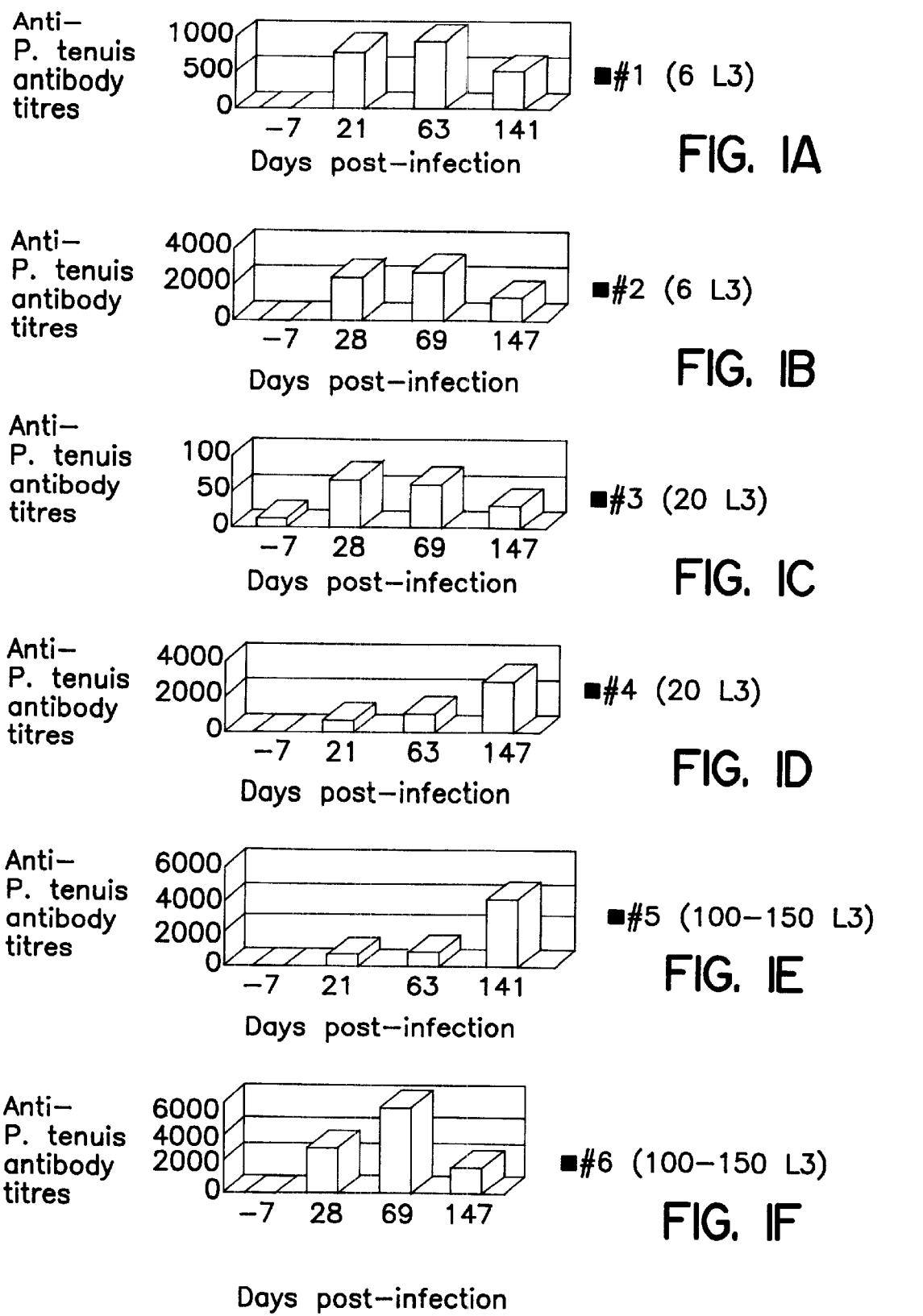
FIG. 1, panels A–F, depict serum titers of anti-Parelaphostrongylus tenuis antibodies in infected white-tailed deer. The legend with each panel refers to the animal by "#" and in parentheses to the number of P. tenuis third-stage larvae (L3) used to infect the animal. Antibody titers were determined in blood samples taken at 7 days pre-infection (−7), 21 or 28, 63 or 69 and 141 or 147 days post-infection, as shown on the x-axis of each graph.

Serum samples collected from six white-tailed deer infected with 6, 20 or 100–150 *P. tenuis* L3 (two animals per dose) contained antibodies that reacted against somatic antigens of *P. tenuis* L3 in ELISA. Anti-*P. tenuis* antibodies were detected within the first month of infection in all animals (FIG. 1), including two animals exposed to as few as six L3 of *P. tenuis* and from which only 3 adult worms were recovered. This early detection indicates that serological testing to detect *P. tenuis* infection can be used earlier than the currently used Baermann technique since none of the infected animals passed L1 in the feces before 90 dpi.

Early antibody titers ranged from 1 in 70 to 1 in 2830 while peak antibody titers ranged from 1 in 70 to 1 in 5700. In comparison, antibody titers of both un-infected, control animals were less than 1 in 10. Animals infected with higher numbers of parasites tended to produce higher peaks of anti-parasite antibodies®=0.88; p<0.05) and higher total antibody levels®=0.85; p<0.05). At necropsy, 3 adult *P. tenuis* were recovered from each of 2 WTD (#1 and 2) given doses of 6 L3 each, 7 and 14 from the animals (#3 and 4) each given 20 L3, and 52 and 32 from the animals (#5 and 6) each given 100–150 L3. In all infected animals, anti-*P. tenuis* antibody titers persisted throughout the course of the experiment.

Such a high sensitivity is important since WTD with natural *P. tenuis* infections usually have less than 10 adult worms in the cranium, even in enzootic areas (Anderson, 1992). Slomke et al. (1995) reported a low level of infection with a mean number of 3.2 adult worms (max 13) among 311 WTD. The number of adult worms harbored by older animals (i.e., 2–6 years and 7–15 years) was not statistically higher than that of younger animals (i.e., $\leq$ one year old and younger) suggesting that WTD in enzootic areas ingest a small number of *P. tenuis* L3 in their first year and do not acquire additional *P. tenuis* afterwards. This is evidence for the existence of concomitant immunity in *P. tenuis* infection: WTD exposed to, and harboring *P. tenuis* worms are protected against the establishment of a newly acquired L3. Re-exposure to the parasite, even when this does not result in a new infection, should help boost the antibody response and make sero-diagnosis of *P. tenuis* infection more likely in enzootic areas.

In four out of the six WTD, antibody levels peaked between day 21 and 69 and then decreased toward the end of the experiment while in the remaining two animals, the highest levels of antibodies amongst the WTD were observed at the end of the experiment.

As expected, anti-L3 antibodies persisted throughout the course of infection in all animals. Without being bound by one theory, this appears to be due to the cross-reactivity between certain L3 and mature parasite antigens. The persistence of anti-L3 antibodies in WTD after L3 have developed into adults, evidences that certain antigens might be shared between L3 and later stages of the parasite. The longevity of antibodies may also contribute to their persistence in the infected animals. A serological test utilizing only a unique antigen present in both L3 and adult should show a progressive increase in anti-parasite titers in infected animals.

Figure 2:
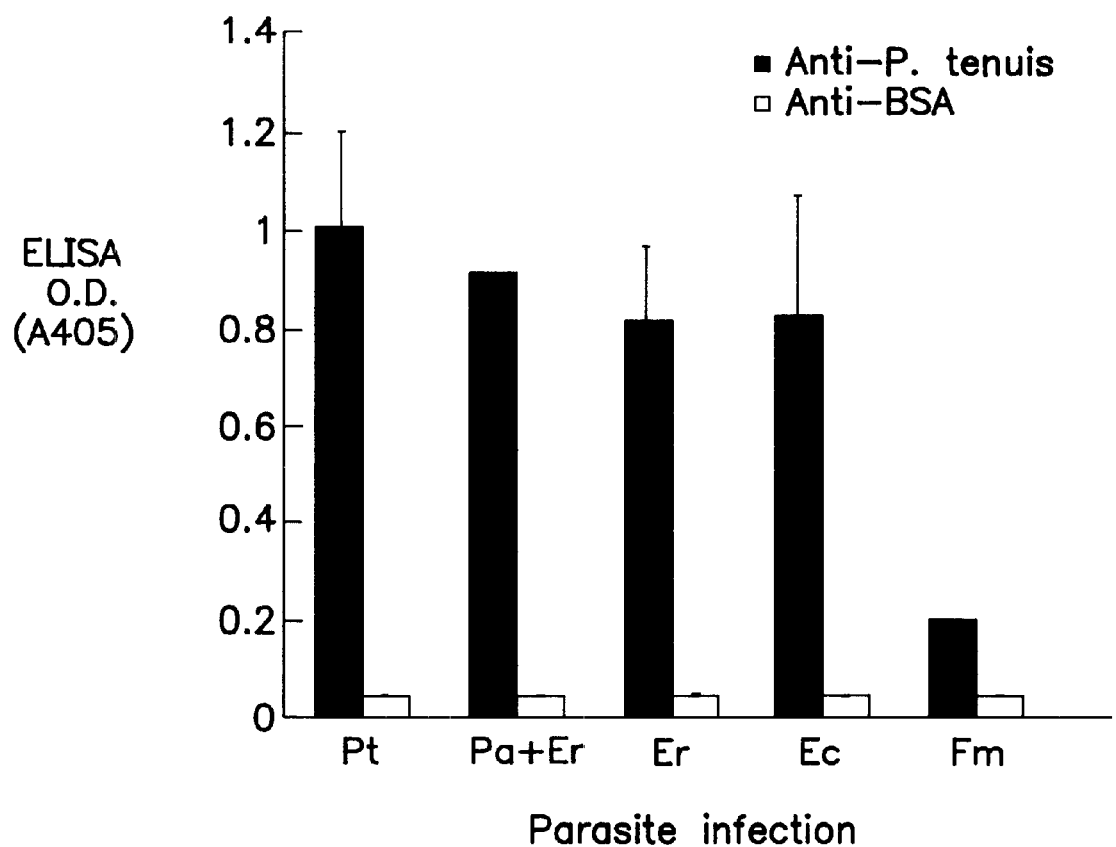
FIG. 2 is a graph depicting reactivity of sera from helminth-infected cervids against somatic antigens of P. tenuis L3. Sera from caribou infected with P. andersoni and E. rangiferi (n=1) or E. rangiferi (n=3), red deer infected with E. cervi (n=3) and elk infected with Fascioloides magna (n=1) were compared with serum from P. tenuis infected white-tailed deer (n=6) for reactivity against somatic antigens of P. tenuis L3 (dark bars) by ELISA. Each serum sample was also tested for reactivity against an irrelevant antigen, bovine serum albumin (light bars). Error bars represent standard deviations from the mean.

Serum samples from caribou infected with *E. rangiferi* or concurrently with *P. andersoni*, and from red deer infected with *E. cervi* also reacted strongly against somatic L3 antigens with intensities similar to that of *P. tenuis*-infected animals (p>0.05; FIG. 2). The serum sample from the Fascioloides-infected elk showed a much reduced cross-reactivity with *P. tenuis* L3 antigens.

1.B.2. Anti-*P. tenuis* Antibodies Specifically Recognized A 37 kDa Protein

Figure 3:
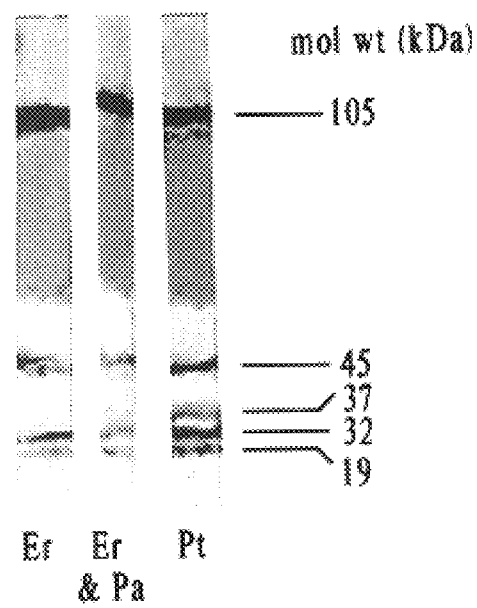
FIG. 3 is a reproduction of a photograph showing immunoblotting of L3 nematode lysates with sera from infected WTD. The right lane shows unique recognition of a 37 kDa P. tenuis antigen by serum from infected white-tailed deer.

The presence of a unique *P. tenuis* antigen was investigated by comparing the profile of somatic antigens of *P. tenuis* L3 recognized by serum antibodies from a *P. tenuis*-infected WTD to those recognized by the serum antibodies from a caribou infected with *E. rangiferi*, and a second caribou infected with *E. rangiferi* and *P. andersoni* concurrently. All three serum samples recognized distinct *P. tenuis* antigens of approximate mol. wt. 105, 45, 32 and 19 kDa, however only the WTD serum uniquely reacted with a *P. tenuis* L3 antigen of approximate mol. wt. 37 kDa (FIG. 3).

Previous efforts to develop a reliable serological test for *P. tenuis* have been plagued by low sensitivity and poor specificity. Dew et al. (1992) used the ELISA technique to demonstrate anti-*P. tenuis* antibodies in the serum and cerebrospinal fluid (CSF) of goats, and in the CSF of deer exposed to 50 *P. tenuis* L3 but failed to detect antibodies in the serum of infected WTD. This poor sensitivity could be attributed to the use of unfractionated antigens from adult worms. Unfractionated L3 antigen preparation appears to be more sensitive than unfractionated adult worm preparations. Furthermore, the poor sensitivity as demonstrated by high OD backgrounds observed in that study may have resulted from the use of high serum concentrations (1 in 8 dilutions).

The use of such dilutions may have been unavoidable given that caprine conjugates rather than cervid conjugates were used in the ELISA. Many helminths share identical or closely related antigens resulting in cross-reactions or non-specific reactions (Almond and Parkhouse, 1985) thereby limiting the usefulness of a serological test. Neumann et al. (1994) showed that anti-*P. tenuis* antibodies may cross-react with even phylogenetically distant parasites like *Trichinella spiralis*. The challenge of test specificity assumes greater importance when the parasite of interest is phylogenetically more closely related to other parasites present in the same geographical area and has similar morphological characteristics and host preferences. Thus, it is important to differentiate cervids infected with *P. tenuis* from those infected with other related nematodes such as *P. andersoni* and *E. rangiferi* which are also present in North America and infect similar hosts. Indeed, when serum collected from caribou infected with *P. andersoni* and *E. rangiferi* were tested, they were found to cross-react strongly with *P. tenuis* somatic L3 antigens proving that a serological test for *P. tenuis* based on unfractionated, somatic L3 antigens will suffer from problems of nonspecificity. As described herein, the use of the 37 kDa fraction as the sole antigen provides a more specific test since serum samples from caribou infected with *P. andersoni* or *E. rangiferi* did not recognize the antigen by the Western blot technique. Failure to detect the 37 kDa antigen may be due to the absence of corresponding antibodies in the caribou sera rather than a technical limitation with the use of anti-deer conjugate since deer and caribou both belong to the sub-family Odocoilinae and the conjugate reacted similarly with deer IgG and caribou IgG in both ELISA and Western blot.

1.B.3. Adult *P. tenuis* Somatic Antigen Preparation Contains Unique 37 kDa Protein The presence of the unique 37 kDa antigen in the adult stage of *P. tenuis* recognizable by serum from *P. tenuis*-infected WTD was assessed by immunoblotting. Infected WTD serum recognized a total of 6 adult *P. tenuis* antigens of which 3 antigens of approximate molecular weights 75, 37 and 20 kDa were specifically and uniquely recognized (FIG. 4). About 9% reactivity in the WTD serum was directed against the 37 kDa antigen as assessed by densitometric analysis. Two antigens of high molecular weights, 158 and 105 kDa, reacted nonspecifically with uninfected and infected WTD serum samples. A 45 kDa protein present in *P. tenuis*, *E. cervi* and *E. rangiferi* was recognized by serum collected from an infected deer but not by serum collected before infection.

Bienek et al. (1998) recently demonstrated extensive cross-reactivity of anti-*P. tenuis* antibodies with Dictyocaulus antigens. Serum collected from a WTD harboring Dictyocaulus prior to experimental *P. tenuis* infection, reacted strongly with the 120 and 180 kDa P. tenuis antigens but not with the 37 kDa antigen. Similarly, Neumann et al. (1994) showed that serum from a *P. tenuis*-infected elk which had a prior, natural *D. viviparus* infection reacted with a 36 kDa protein present in *P. tenuis* but not in *D. viviparus*. An antigen of the same molecular weight (37 kDa) as the unique L3 antigen was detected in the adult parasite.

The concentrations of 37 kDa antigens present in the L3 and adult stages are not precisely known but appear to be low. When analyzed by SDS-PAGE, *P. tenuis* L3 and adult contain 17 and 18 protein bands, respectively. The mean concentration of proteins in *P. tenuis has been estimated at* 0.11 $\mu$g per L3 and 140 $\mu$g per adult. Based on densitometric analyses of SDS-PAGE gels, the 37 kDa antigens constitute 5.8% of somatic L3 antigens and 5.5% of somatic adult antigens. These proportions represent estimates of the maximum concentrations of the antigens in each worm stage, but actual concentrations may be lower, since a protein identified by inmmuno-staining may not be the only protein constituent of a band of the corresponding molecular weight in an SDS-PAGE gel.

Example 2
Evaluation of Excretory-Secretory Products And Somatic Worm Antigens For Diagnosis of P. tenuis Infections Serological diagnosis of infection based on the demonstration of antibodies present in an infected animal relies on the availability of good quality antigen. The sensitivity of a serological test, i.e., how well it detects an infected animal, and the specificity, i.e., how well it correctly identifies animals free of the infection is largely dependent on the quality of the antigen. (Welch et al. (1991)). The ideal choice of an antigen for serological diagnosis of infectious diseases is one against which all infected animals produce an early and persistent antibody response. Uninfected animals and those infected with other agents should fail to produce antibodies against the antigen. Furthermore, in nematode infections where the parasite often undergoes a multistage development in the host, the antigen should react with antibodies produced by the host in response to the different stages of the parasite. In order to develop a sensitive and specific serological test for WTD infected with P. tenuis, three antigen preparations from P. tenuis were prepared and evaluated, namely the excretory-secretory products of L3 (ES-L3) and larval and adult somatic antigens (sL3 and sA).

2.A. Materials And Methods
2.A.1. Parasites

Third-stage larvae (L3) of P. tenuis, obtained from pre-exposed snails (Triodopsis multilineata) according to described methods were used to infect white-tailed deer. (Lankester (1996)). For antigen preparation, the L3 were either cultured to produce excretory-secretory products (ES-L3) in vitro or used to prepare somatic antigens (sL3). Adult P. tenuis were obtained from the meninges of experimentally infected white-tailed deer at postmortem and used for preparing somatic antigens (sA). (Slomke et al. (1995)).

2.A.2. Preparation of Parasite Antigens

L3 or adult P. tenuis were cleaned and washed in PBS, resuspend in 1 ml of PBS and kept on ice. Parasites were sonicated with a Braunsonic sonicator (Braunsonic Melungen, Allentown, Pa.) at 300 W for 1 min at a time for a total of 5 min after which the parasite suspension was transferred into a microfuge tube and spun at 12,000 rpm for 5 min. The supernatant was kept at −20° C. Protein concentrations were determined using the BCA kit (Pierce, Rockford, Ill.).

ES-L3 antigens were produced in a serum-free environment according to published procedures of Call et al. (1995) with some modifications. Briefly, L3 parasites were suspended in RPMI-1640 (RPMI), transferred into a sterile dialysis bag which was knotted at the ends and placed in a petri dish containing RPMI supplemented with 10% fetal calf serum (FCS). Parasites were cultured at 37° C. and 5% $CO_2$ incubator (VWR, Plainfield, N.J.) and every 24 hr thereafter, the contents of the dialysis bag were carefully aspirated, spun at 12,000 g for 5 min, and the supernatant kept as ES antigens. To reduce the extent of contamination of ES-L3 by somatic antigen from degraded parasites, cultures were monitored to assess the mortality of L3. Mortality was found to be less than 5% for the first 7 days of uninterrupted culture. Dead and dying parasites were removed every 24 h. In addition, optical density of harvested ES-L3 was measured at wavelength 260 nm to assess nucleic acid contamination and, by implication, the extent of contamination by degraded parasites. Nucleic acid contamination was found to be negligible.

2.A.3. Infection of White-tailed Deer with P. tenuis and Blood Collection

The six WTD used in experiments were acquired as week-old orphaned fawns in Saskatchewan where P. tenuis does not occur and raised in captivity (Anderson et al. (1981)). They were bottle-fed and held in an open paddock until being transported to Thunder Bay, Ontario, where they were held on clean concrete and experimentally infected with P. tenuis L3. All animals were 9.5 months old at the start of the experiment. Two deer were each given 6 larvae (#1 and 2), 2 were given 20 (#3 and 4), and 2 were given between 100 and 150 (#5 and 6). Blood samples were collected from each of the WTD 1 wk before infection and at different times after infection until the end of the experiment at 147 days post-infection (dpi). All 6 WTD passed small numbers of Dictyocaulus larvae in their feces during the experiment but no adult specimens could be recovered at necropsy.

2.A.4. ELISA

Antigens (ES-L3, sL3 or sA) were diluted in PBS and adsorbed to wells of a microtitre plate (Dynatech Laboratories, Chantilly, Va.) at 1 µg/well and incubated at 37° C. overnight, following which wells were washed with PBS containing 0.5%Tween 20 (PBST). Serial dilutions of WTD serum in PBST were applied to the microtitre plate wells and incubated at 37° C. for 3 h. At the end of the incubation, plates were washed and rabbit anti-white-tailed deer IgG (Kirkegard and Perry Laboratories, Gaithersburg, Mass.) diluted in PBST (1:2,000) applied to each well. After a 2 hour incubation at 37° C., wells of the plate were washed with PBST, phosphatase substrate (Kirkegard and Perry Laboratories, Gaithersburg, Mass.) applied and allowed to react for 1 h. Development was stopped with 5% EDTA and the optical density (OD) read at 405 nm with a spectrophotometer (Labsystems, Finland). For this analysis, serum samples were divided into two batches so that each parasite dose was tested in each batch i.e., deer #1, 3 and 5 in the first batch and deer #2, 4 and 6 in the second batch. Serum samples from each batch were all tested at the same time, against ES, sL3 or sA antigens. Each sample was analyzed at least thrice and the results were found to be highly reproducible. In addition, to ensure proper comparison in the presence of possible inter-plate variation, runs were designed such that in one case, the same microtitre plate was coated with the three different antigens and reacted against serum samples from animals infected with the different doses to see whether the trend observed was consistent. In another run, each antigen was used to coat a single plate and all six serum samples were tested at the same time. Inter-plate and day-to-day variations were found to be less than 10%, therefore, results from one representative batch run is presented. A post-infection serum sample was scored positive if the ELISA OD value is equal to, or greater than, twice the OD value of the corresponding pre-infection serum sample. Statistical significance was analyzed at the 99% confidence limits.

2.A.5. SDS-PAGE and Immunoblotting

Parasite antigens (crude L3 stage or adult worm antigens) were separated on a 10% SDS-PAGE at 160 V for 45 min, under reducing conditions. The separated proteins in the gel were photographed following staining with BioRad Silver stain plus kit (BioRad, Hercules, Calif.) or alternatively, the proteins were transferred onto nitrocellulose membrane (BioRad, Hercules, Calif.) for immuno-staining. Membranes with proteins were blocked with PBS containing 5% milk (i.e., PBS-milk) for 30 mins and washed with PBS containing 0.1% Tween 20 (PBS-T). WTD serum samples (preinfection and 141 dpi) diluted 1 in 25 in PBST containing 2.5% milk (i.e., PBST-milk) were applied to membrane strips, and incubated overnight. Subsequently, the membrane was washed with PBST and alkaline phosphatase-labeled rabbit anti-deer IgG diluted 1 in 500 in PBST-milk added. After 4 hours of incubation, the membrane was washed three times in PBST and then a final wash in PBS. Color development$^{reagent}$ (BCIP/NBT phosphatase substrate) was added to the membrane and incubated in the dark. Color development was stopped after 30 min by the addition of tap water to the membrane.

2.B. Results

2.B.1. Comparative Sensitivities of Indirect ELISAs Utilizing ES-L3, sL3 or sA Antigens in the Diagnosis of *P. tenuis* Infections in WTD The ES-L3 antigen had the highest sensitivity as demonstrated by the strongest intensity of reaction, earliest detection of antibodies and lowest background. ES-L3 consistently detected anti-*P. tenuis* antibodies in all infected animals starting from the first month of infection until the end of the experiment (FIG. 5). The ELISA OD values of pre-infection. sera (background OD) were consistently less than 0.14 (mean=0.09). Antibodies against ES-L3 increased quickly following infection and attained a peak within the first month of infection (4 out of 6 animals) or soon after and often remained stable at this level (5 out of 6 animals). Peak ELISA OD values of sera from the infected deer were between 0.74 to 1.28 (mean=1.00).

The sensitivity of ES-L3 antigen in detecting antibodies to *P. tenuis* may be a consequence of the unique immunological reaction of hosts to parasitic infections. Unlike viruses and bacteria that multiply and undergo tremendous turnover in an infected host, nematodes do not divide and while some infecting parasites may die, many that survive to the adult stages will remain intact for a long period and may not be exposed to the immune system. *P. tenuis* may live for many years (Slomke et al. (1995)), *Elaphostrongylus cervi* for 6 years (Watson (1984)) and *P. odocoilei* for 9.4 years (Samuel W. M, personal communications). Thus, the main immunological recognition of a parasite by the host may be via the ES-L3 products produced by the parasite and consequently, the predominant immune response directed against the ES products.

Similar to ES-L3 antigen, the sL3 antigen consistently reacted with anti-*P. tenuis* antibodies in all infected animals throughout the course of infection. Anti-sL3 antibodies were also detectable in response to infection from the first month (FIG. 5). The background OD levels for sL3 ranged from 0.15 to 0.35 (mean =0.21). Peak ELISA OD values ranged from 0.47 to 0.78 (mean=0.66). Anti-sL3 antibodies decreased terminally in 4 of 6 infected animals, but remained detectable in all animals until the end of the experiment. The presence of anti-sL3 antibodies late in the infection and at a time when L3 stages would have matured into adult forms may be explained by two different events. First, it appears that the anti-sL3 antibodies are long-lived as supported by the finding that serum collected at the termination of the experiment, and used in immunoblotting, recognized an antigen (M. Wt.=40 kDa.) present in the somatic antigen preparation of larvae but not in the adult worm preparation. Second, cross-reacting antigens present in adult antigens may boost the initial anti-sL3 response as suggested by the possible recognition of 37 kDa antigens in larval and adult antigen preparations.

In contrast to ES-L3 and sL3, the sA antigen detected anti-*P. tenuis* antibodies in 4 infected animals but not in two animals (#1 and 3) infected with 6 and 20 parasites (FIG. 5). In one animal (#3), the background OD value (=0.55) was higher than the OD value of any of the post-infection sera collected on 4 different occasions between 28 and 141 dpi (OD range=0 .35 to 0.4). The background OD for sA antigen ranged from 0.16 to 0.55 (mean=0.30). The peak OD values ranged from 0.37 to 0.75 (mean=0.5). Non-specific background reactions accounted for 9% of the anti-ES, 32% of anti-sL3, and 60% of anti-sA reactivities.

Thus, the sA antigen was the least sensitive antigen preparation. It detected anti-*P. tenuis* antibodies within one month of infection in two animals (#2 and 5), after the first month in two other animals (#4 and 6) and at no time throughout the course of infection in the two remaining animals (#1 and 3). Even among the positive animals, the intensity of reaction as assessed by OD readings, was relatively low. These observations confirm previous suggestions (Bienek et al. (1998); Neumann et al. (1994)) that adult somatic antigens may not be very useful in the diagnosis of *P. tenuis*. The effectiveness of ES products from the adult worm could not be assessed because live adult worms were not available at the time of the study.

ES-L3 provided the greatest discrimination between the ELISA OD values of pre- and post-infection sera. ES-L3 detected antibodies to *P. tenuis* in all infected animals within the first month of infection and at all sampling times thereafter. The intensity of the earliest reactions was higher with ES-L3 than sL3. ES-L3 appears to be superior to either sL3 or sA in the diagnosis of *P. tenuis* infection since anti-ES-L3 antibodies were induced very quickly in infected animals and were generally maintained at stable high levels during the course of the experiment.

In order to test which antigen could most sensitively detect the early presence of WTD anti-*P. tenuis* antibodies, serum samples collected prior to infection, and at 14 or 28 dpi were tested against ES, sL3 or sA antigen by indirect ELISA. ES-L3 and sL3 detected anti-*P. tenuis* antibodies in serum at 14 dpi (FIG. 2). Furthermore, ES-L3 and sL3 showed a fourfold increase in the intensity of reaction between pre-infection and the serum sample collected 14dpi. The sA antigen failed to detect antibodies in infected animals at day 14 dpi. The intensity of the early reaction (14 and 28 dpi) was highest for ES-L3 and lowest for sA.

Anti-ES-L3 antibodies were detectable by ELISA and Immunoblotting at the terminal stages of the experiment. Anti-ES-L3 antibodies, similar to anti-sL3 antibodies, persisted in all infected animals long after the L3 stages would have moulted into advanced stages, and by implication, the cessation of ES-L3 production. The persistence of antibodies could be explained by mechanisms similar to that of anti-sL3: longevity of antibodies and identical antigens produced by more advanced parasite stages.

The suitability of the sL3 in serological diagnosis of *P. tenuis* may be attributed to the common antigens present in the infective L3 stage and their ES products. Interestingly, infected WTD serum recognized at least three antigens present in ES-L3 but not in sL3, suggesting that once these antigens are produced by L3, they are completely excreted. This observation discounts the possibility of significant cross-contamination of the ES-L3 antigen preparation by sL3 antigen. An antigen found to be abundant in the ES products while apparently undetectable in the somatic antigen preparation may be more appropriately described as an excretory antigen while an antigen shared between the ES products and the somatic antigen preparation may be described as a secretory antigen.

2.B.2. Cross-Reactivity of ES-L3. sL3 and sA With Sera from Cervids Infected with Other Parasites ES-L3, sL3 and sA showed significant cross-reactivity with sera from red deer infected with *E. cervi*, and from caribou infected with *E. rangiferi* only, or concurrently with *P. andersoni* (FIG. 7). The ES-L3 showed the strongest cross-reactivity among the three antigen preparations. Serum from *E. rangiferi*-infected caribou showed the least, but nevertheless significant, cross-reactivity.

All three antigen preparations show low specificity as demonstrated by high cross-reactivity with sera from cervids infected with parasites closely related to *P. tenuis*, namely *P. andersoni*, *E. rangiferi* and *E. cervi*. The observed cross-reactions are indications of the similarities between some antigens of *P. tenuis* and those found in the other parasites. The report that *P. tenuis* share as many as 5 antigens with *Trichinella spiralis* (Family: Trichuridae) and resulting in cross-reactivity between these two parasites (Neumann et al., 1994) further illustrates the challenges of developing a specific serological test not only for *P. tenuis* but for parasites, using unfractionated antigens. Thus, in spite of the sensitivity of ES-L3 or sL3 antigens, it is evident that unfractionated *P. tenuis* antigen may not be useful for field identification of *P. tenuis*-infected cervids. It is therefore imperative to identify individual antigen(s) unique to the parasite. As described in Example 1 above, identification of a unique 37 kDa protein of *P. tennis* that reacts with *P. tenuis*-infected WTD serum but not sera from cervids infected with *E. rangiferi*, *P. andersoni* or *E. cervi* is described. A protein of about 37 kDa size appears to be present in all three antigen preparations (FIG. 9). It is not clear why the 37 kDa in the adult antigen failed to produce a positive result in animals #1 and 3; possible explanations include low levels of antibodies in infected animals or high non-specific reactivity of pre-infection sera to other antigens. A more probable reason is the complexity of the adult antigen preparation, as shown by a higher number of individual antigens than for the larval antigens, which may be a confounding factor for specific antigen-antibody interactions. The nature of the antigen appears to determine the extent of false positive serological results (see, e.g, Gamble et al. (1993).

In sum, previously untested excretory-secretory products from *P. tenuis* showed the best sensitivity and may be used, as the larval somatic antigens, for monitoring experimental *P. tenuis* infections.

2.B.3. SDS-PAGE Analysis of ES-L3, sL3 or sA

Electrophoretic separation of the antigens done to analyze the complexity and the size compositions of individual proteins present in each of the antigen preparations showed that the ES-L3 antigen preparation had the least number of protein bands and sA the most. Six protein bands were detected in the ES-L3 with a m. wt. range of 2–72 kDa. The sL3 had 15 protein bands with a m. wt. range of 14–97 kDa while sA had 26 protein bands and a m. wt. range of 14–116 kDa. (FIG. 8).

2.B.4. Western Blot Analysis of *P. tenuis* -Infected Serum Against ES-L3, sL3 or sA Infected deer serum recognized antigens of different sizes in each antigen preparation, however, a 37 kd appeared to be the only protein consistently recognized by *P. tenuis* -infected deer serum in all three antigen preparations. As in the ELISA, the highest background reaction observed in Western blot was with sA (FIG. 9).

Thus, antigens of the third-stage larva may be more relevant than those from adults in the serodiagnosis of *P. tenuis* and furthermore, excreted and secretory antigens are more sensitive than the somatic antigens of the third-stage larvae.

Example 3
Construction, Screening of cDNA Library and Identification of Parasite Genes

3.A. Materials And Methods

3.A.1. Isolation of *P. tenuis* RNA

Adult *P. tenuis* worms (males and females) were washed three times in phosphate buffered saline (PBS, pH 7.4) and disrupted by passing through the barrel of a syringe and applied to a shredder (Qiagen, Santa Clarita, Calif.) according to the manufacturers instructions. Total RNA was isolated from disrupted *P. tenuis* worms using the RNeasy mini kit (Qiagen, Santa Clarita, Calif.).

3.A.2. Antiserum

Mouse anti-*P. tenuis* antiserum was produced by immunization of ten mice with sonicates of *P. tenuis* adult worm. White-tailed deer (WTD) anti-*P. tenuis* antiserum was obtained from a white-tailed deer infected with 100 *P. tenuis* third-stage larvae. Serum obtained from the WTD before infection was used as control (normal) serum. Elk anti-Dictyocaulus antiserum was obtained from an elk naturally infected with *Dictyocaulus viviparus*. Rabbit anti-*E. cervi* antibodies was produced by immunizing a rabbit with sonicated adult *E. cervi*.

3.A.3. Construction of cDNA Library

*P. tenuis* cDNA was synthesized using a cDNA kit, and a library constructed with the UNIZAP vector (Stratagene, La Jolla, Calif.), according to the manufacturer's instructions. Using total RNA as starting material, *P. tenuis* messenger RNA was reverse transcribed to first strand cDNA by use of XhoI linker-poly(dT) primer, Moloney murine leukemia virus (MMLV) reverse transcriptase, and a ribonuclease inhibitor at 37° C. for 1 hour. Second strand CDNA was synthesized by *Escherichia coli* DNA polymerase following the generation of nicks in RNA of the first strand cDNA-RNA duplex by RNase H. CDNA synthesis was monitored by the addition of radioactive nucleotides in control reactions containing aliquots of the first or second-strand reaction mix. The synthesized, double-stranded CDNA was blunt ended with cloned pfu DNA polymerase at 72° C. for 30 minutes, ligated to EcoRI adapters with T4 DNA ligase at 4° C. for 48 hours, and digested with XhoI at 37° C. for 1.5 hours, resulting in CDNA with an XhoI cohesive 5' end, and an EcoRI cohesive 3' end.

The CDNA was separated according to size by chromatography on Sepharose CL-2B, and larger sized cDNA fragments were ligated unidirectionally into a UNIZAP vector that was predigested with XhoI and EcoRI, and packaged into Gigapack III Gold packaging extract (Strategene). The titer of, and the percent recombinants in, the primary library were determined by infecting *E. coli* XLI-Blue MFR with an aliquot of the CDNA-UNIZAP library (phage), and mixing with 0.7% agarose-LB (Top agar), Isopropyl-1-thio-β-D-galactopyranoside (IPTG) and 5-Bromo-4-chloro-3-indolyl-β-D-galactopyranoside (X-gal) before plating on a NZY agar plate. The primary library was amplified once in *E. coli* XLI-Blue MRF and stored at −70° C.

3.A.4. Immunoscreening of cDNA Library

Primary screening of the amplified cDNA-UNIZAP library was done with hyperimmune mouse anti-*P. tenuis* (adult worm) antiserum. First, the cDNA-UNIZAP library was plated at an average density of 4,500 PFU per 150-mm agar plate, and in cubated at 37° C. for 5 h or until plaques are barely visible. Nitrocellulose, pre-soaked in 10 mM IPTG solution was applied to the plate and incubated for a further 4 h. The membrane was removed, rinsed in PBS, pH 7.4, and placed in a blocking solution of PBS containing 20% fetal calf serum (CS) for 2 h at room temperature. Following the blocking step, nitrocellulose was rinsed in PBS and incubated at room temperature, overnight, in mouse antiserum solution (1:000) in PBS containing 0.1% Tween 20 (PBST). Nitrocellulose was washed in PBST, thrice and placed in a solution of peroxidase-labeled rabbit anti-mouse Ig, diluted 1:1000 in PBST and allowed to react for 4 h at room temperature. At the end of the incubation, nitrocellulose was washed three times in PBST and developed with phosphatase substrate (5-Bromo-4-chloro-3-indolyl-phosphate-Nitro Blue Tetrazolium, Kirkegaard & Perry Laboratories, Gaithersburg, Md.).

3.A.5. Identification of Positive Clones

Positive reacting plaques were picked by orientating marked nitrocellulose against the agar plate and picking the plaques as an agar plug with the end of a sterile pasteur pipette. Phages in the plug were eluted into SM buffer (50 mM Tris, pH 7.5 containing 0.1 M NaCl,0.01% gelatin) by overnight incubation on a shaker. Eluted phages were plated and re-screened as above until a population of uniformly reacting positive clones were obtained. Each positive clone was amplified and stored at −70° C. Further screening of clones was done with serum from $P.$ $tenuis$-infected white-tailed deer. The specificity of antigen expressed by the putative clones was assessed by using sera specific for other parasites (red deer anti-$Elaphostrongylus$ $cervi$, elk anti-$Dictyocaulus$ $viviparus$) on the nitrocellulose.

3.A.6. PCR Amplification of Positive Clones

Confirmation of the presence of, and the determination of the size of insert in each clone, were done by PCR of the multiple cloning site of the UNIZAP vector between the T3 and T7 sequences. The PCR reaction consists of lysis of cDNA-lNIZAP clone ($10^7$ phages) at 95° C. for 5 min followed by annealing of the vector DNA with T3 and T7 primers (0.5 M per primer) at 55° C. for 5 min. Hot-start PCR was performed using Taq polymerase (AmpliTaq, Perkin Elmer) activated at 95° C. for 10 min and reaction mixture was subjected to each of 40 cycles consisting of a primer extension (72° C., 90 s), denaturation (94° C., 30 s), annealing (55° C., 75 s) and a final primer extension step (72° C., 10 min).

3.A.7. Sizes of Cloned $P.$ $tenuis$ Genes

The size of the cDNA insert present in each UMZAP-cDNA clone was determined by PCR amplification of the insert using T3 and T7 primers which bind regions of the UNIZAP vector at either ends of the insert. UNIZAP-cDNA clone 128, 175, 212, and 323 were previously demonstrated to produce proteins that react with anti-$P.$ $tenuis$ antibodies. Clone 212 also reacted with anti-$E.$ $cervi$ antibodies. Clones of UNIZAP vector only (i.e., without insert=1', 2' and 3') were included as controls. Aliquots (10 μl) from the PCR reaction tubes were analyzed on 0.7% agarose gels and visualized by ethidium bromide staining.

3.B. Results

3.B.1. $P.$ $tenuis$ RNA

Between about 21 and about 25 μg of total RNA was extracted from a total of 6 adult $P.$ $tenuis$ worms.

3.B.2. cDNA Synthesis

The synthesized cDNA ranged from 0.1–4 kb in length. FIG. 10 shows the messenger RNA component of $P.$ $tenuis$ total RNA was transcribed into first (Lane 1) and second (Lane 2) strand CDNA using MMLV reverse transcriptase. cDNA synthesis was monitored by the incorporation of radioactive nucleotides, agarose analysis and visualization by radiographic analysis. In FIG. 10, M=λ-HindIII molecular weight marker.

3.B.3. Size of $P.$ $tenuis$ cDNA Library

Following the ligation of $P.$ $tenuis$ cDNA with the UNI-ZAP vector to create the $P.$ $tenuis$ cDNA-UNIZAP primary library, the titre of the library was estimated at $1.13 \times 10^5$ clones.

3.B.4. Immunoreactive $P.$ $tenuis$ Clones

Thirteen clones were found to react with mouse anti-$P.$ $tenuis$ antiserum. FIG. 11 shows identification of $P.$ $tenuis$ cDNA clones from primary screening with mouse anti-$P.$ $tenuis$ antiserum and re-screened with other sera/antisera (2. WTD anti-$P.$ $tenuis$, 3. WTD normal serum, 4. Elk anti-Dictyocaulus) to assess cross-reactivity or uniqueness of clones. Four of the clones, 191, 210, 212 and 222 reacted with mouse anti-$P.$ $tenuis$ and rabbit anti-$E.$ $cervi$ antibodies.

FIG. 12 shows screening of amplified $P.$ $tenuis$ cDNA-UNIZAP library on nitrocellulose with mouse anti-$P.$ $tenuis$ antiserum to identify $P.$ $tenuis$ antigen-producing clones. $E.$ $coli$ XLI was infected with $6 \times 10^3$ $P.$ $tenuis$ cDNA-UNIZAP phages of the amplified library, and grown on an NZY plate. Plaques produced by the lysis of bacteria were transferred to nitrocellulose and the presence of putative $P.$ $tenuis$ antigens identified with the antiserum. One plaque (arrow in FIG. 12) produced antigen that reacted with anti-$P.$ $tenuis$ antiserum.

Size of $P.$ $tenuis$ Genes

The size of the $P.$ $tenuis$ genes that produce antigens that reacted with anti-$P.$ $tenuis$ antiserum as well as anti-$E.$ $cervi$ antiserum, as determined by PCR is as follows:

| Clone | Size of gene (bp) |
|---|---|
| 191 | not determined |
| 210 | 575 |
| 212 | 875 |
| 222 | 1,375 |

In addition, FIG. 13 shows the size of cDNA inserts present in UNIZAP-clones 128, 175, 212 and 323 as determined by PCR amplification using T3 and T7 primers. The lane labeled "V1" is the molecular weight marker. Lanes labeled 1', 2' and 3' are UNIZAP vector only controls. The size of the $P.$ $tenuis$ gene PCR produce minus the contribution of primers and vector nucleotides. All clones produce polypeptides that react with anti-$P.$ $tenuis$-antibodies. Clone 212 also reacted with anti $E.$-$cervi$ antibodies.

Thus, polynucleotides encoding Protostrongylidae antigens (both common and $P.$ $tenuis$-specific antigens) were isolated, sized and screened for reactivity.

Example 4

Serological Diagnosis of $Elaphostrongylus$ $Cervi$ Infection and Identification of a Unique $E.$ $Cervi$ Antigen 4.A. Materials And Methods 4.A.1. Parasites And Sera Red deer were infected with the L3 stages of $E.$ $cervi$ obtained following published methods (Gajadhar and Tessaro (1995) J of Parasitology 81:593–596). Originally, first-stage larvae of $E.$ $cervi$ obtained from infected red deer in New Zealand were exposed to laboratory-reared snails ($Triodopsis$ $multilineaia$) and slugs ($Deroceros$ $reticulatum$) and the third stage larvae obtained from the gastropods were used to infect red deer. Six weeks after exposure, slugs or snails were placed in a 300 μl sieve (Canadian Standard Sieve Series, W S Tyler, St. Catharines, Ontario, Canada) and immersed in a beaker of 250 ml of 0.7% pepsin in water containing 0.8% HCl at 37° C. for 1 h. At the end of the incubation, the L3 present in the pepsin-HCl were allowed to sediment, washed 3 times in water, picked individually under a dissecting microscope (Leica MS5, Heerbrugg, Switzerland) and counted.

4.A.2. Animals and Infection

Orphaned red deer fawns kept in isolation were bottle-raised and weaned onto a pelleted ration. Animals were infected per os with L3 stages of *E. cervi*. Feces were collected daily from the fawns and analyzed by a modification of the Baermann's procedure for the examination of *E. cervi* L1 (Gajadhar et al. (1994) *Canadian Veterinary Journal* 35:433–437) to detect the onset of passing of larval stages, i.e., patency. Blood samples were collected from the fawn before, and at regular intervals after infection. Animals were restricted in their pens according to the guidelines of the Canadian Council on Animal Care. The care of the animals and the handling of fomites, equipment and deer feces were done according to Institutional guidelines to prevent the contamination of the environment with *E. cervi*.

4.A.3. *E. Cervi* Antigens

ES products: 1000 L3 obtained from slugs or snails and picked clean were cultured in RPMI-1640 containing gentamycin (100 μg/ml) and fungizone (10 μg/ml) at 37° C. and with 5% $CO_2$. At 4 day intervals, culture supernatant containing parasite ES product was removed from the culture and the following protease inhibitors added: EDTA (2 mM), leupeptin (2 μg/ml), pepstatin (1 μg/ml), phenylmethanesulphonyl fluoride, PMSF (100 μg/ml), tosyl-L-lysine chloromethyl ketone, TLCK (50 μg/ml), and tosyl-amido-l-phenylethyl chloromethyl ketone, TPCK, (100 μg/ml). The culture supernatant was spun at 12,000 g for 10 min to sediment insoluble parasite material. The culture supernatant containing ES products was then concentrated using Centricon-3 and Microcon-3 (Mwt cut off=3 kDa; Amicon Inc., Beverly, Mass.). When it is necessary to know the protein concentration of the ES products, protease inhibitors were not added and the culture supernatant was dialyzed against PBS, pH 7.4 overnight at 4° C. before concentration and protein concentration was determined with the aid of the Bicinchoninic acid, BCA, kit (Pierce, Rockford, Ill.).

L3 crude antigens: L3 obtained from slugs or snails (as above) were suspended in PBS and sonicated (Braunsonic, Melsungen A G) at 300 W 1 min, rested for 1 min and repeated until worms were sonicated for a total period of 5 min. At the end of the sonication, no discernable worm fragments were present in the worm suspension which was then transferred into a microfuge tube and spun at 12,000 g for 5 min. The supernatant was kept at −20° C. Protein concentration was determined using the BCA kit.

4.A.4. SDS-PAGE and Immunoblotting

Antigen (ES products or L3 crude antigens) were separated on a 10% SDS-PAGE at 160 V for 45 min, under reducing conditions. At the end of the run, gels were stained with Coomassie stain or Silver stain kit (BioRad, Hercules, Calif.) to visualize the protein bands or alternatively, the proteins in unstained gels were transferred onto nitrocellulose membrane (BioRad, Hercules, Calif.) for immunostaining. Membranes bearing proteins were blocked with PBS containing 5% milk (i.e., PBS-milk). Serum samples (deer or control) diluted 1 in 25 in PBS containing 0.1% Tween 20 (PBS-T) and 2.5% milk (i.e., PBST-milk) were applied to membrane strips and incubated overnight. After incubation, the membrane was washed with PBST and the appropriate conjugate (e.g., alkaline phosphatase-labeled rabbit and anti-deer IgG) diluted 1 in 500 in PBST-milk added. After 4 hours of incubation, membrane was washed three times in PBST and then a final wash in PBS. Color development reagent (BCIP/NBT phosphatase substrate, Kirkegaard and Perry Laboratories, Gaithersburg, Mass.) was added to the membrane and incubated in the dark. Color development was stopped after 30 min by the addition of tap water to the membrane.

4.B. Results

4.B.1. ELISA Anti-*E. Cervi* Antibodies

Serum antibodies to *E. cervi* L3 were detectable in all three infected animals at 23 days post-infection as assessed by indirect ELISA. Antibodies levels increased steadily up to 42–71 dpi and declined thereafter in all animals. Antibodies dropped to undetectable levels by 176 dpi in the animals given 6 parasites. In the other animals, antibodies persisted until the termination of experiment at 176 or 537 dpi.

4.B.2. SDS-PAGE Analysis of the Excretory/Secretory and L3 Somatic Antigens of *Elaphostrongylus Cervi*

Electrophoretic analysis of the constituents of *E. cervi* ES products revealed the presence of 9 protein bands with a broad range of molecular weights (<14.4 to over 200 kDa). In comparison, the L3 consists of as many as 16 protein bands also with a broad range of molecular weights (19.1–97.4 kDa). The ES products contain 2 bands that are significantly greater in sizes than the heaviest L3 antigen band.

4.B.3. Anti-*E. Cervi* Somatic L3 Antibodies

Infected deer serum reacted with eight protein bands of *E. cervi* L3 following separation of crude L3 antigen by SDS-PAGE and immunoblotting. The eight protein bands had a molecular weight range of <19 kDa to 160 kDa under reducing conditions. Serum samples from the animal infected with 100 L3 (Deer #3) showed the most distinct pattern of reactivity. Two parasite proteins band of molecular weights 19 and 35 kDa reacted slightly with pre-infection serum but showed a stronger reaction with post-infection sera collected on day 23 and 211 after exposure to L3. A 45 kDa protein reacted strongly with post-infection sera samples while a 47 kDa protein reacted less significantly and similarly, only with post-infection serum sample. Three protein bands (52–78 kDa) did not react with pre-infection sera but reacted significantly with day 211 post-infection sera but less strongly with post-infection sera collected earlier.

Sera samples collected from deer #2 post-infection detected most of the proteins but to a lesser degree for the larger protein bands of 47 kDa and 52–78kDa. The 19 and 35 kDa bands were detectable by post-infection sera as in deer #3, but were negative for the pre-infection sera.

Deer #1 sera did not react with the 47 kDa protein at any time. The strong staining 35 kDa protein strongly reacted with pre-infection serum sample.

The 35 kDa behaves as an immunodominant antigen and shows very strong cross-reactivity with pre-infection serum sample from one animal (deer #1).

4.B.4. Anti-*E. Cervi* ES Antibodies

Infected deer (#3) sera reacted with 5 distinct ES antigen bands. Two of these antigen bands reacted non-specifically with pre-infection serum, but the intensity of the reaction increased with infected sera samples. The reaction was strongest in sera collected 23 days post-infection. The bands recognized had estimated molecular weights of 37, 42, 45, 63 and 128 kDa. In addition, there was a strong band at the running end of the gel (front dye) which may correspond to a protein size of 19 kDa or less or may represent smaller fragments from any of the bigger proteins. Sera from all 3 infected animals show similar pattern of reactivity with ES antigens. FIG. 14 shows the identification of a unique 52 kDa *E. cervi*-specific antigen.

Although preferred embodiments of the subject invention have been described in some detail, it is understood that obvious variations can be made without departing from the spirit and the scope of the invention as defined by the appended claims.

REFERENCES

Alden C, Woodson F, Mohan R, et al.: 1975, Cerebrospinal nematodiasis in sheep. J. Amer Vet Assoc 166: 784–786.

Almond N M, Parkhouse R M E: 1985, Nematode antigens. Curr Top in Microbiol and Immun 120: 173–203.

Anderson R C: 1964, Neurological disease in moose infected experimentally with *Pneumostrongylus tenuis* from white-tailed deer. Pathologia Vet 1: 289–322.

Anderson R C: 1992, Nematode parasites of vertebrates. C. A. B. International, Oxon, United Kingdom.

Anderson R C, Prestwood A K: 1981, Lungworms. In: Diseases and parasites of white-tailed deer, W R Davidson, F A Hayes, V F Nettles, F E Kellogg (eds.). Tall Timbers Research Station, Tallahassee, United States, p. 266–317.

Anderson R C, Strevile U R: 1967, The penetration of *Pneumostrongylus tenuis* into the tissues of white-tailed deer. Can J Zool 45:285–289.

Behrend D F, Witter J F: 1968, *Pneumostrongylus tenuis* in white-tailed deer in Maine. J Wildl Manage 32: 963–966.

Bienek D R, Neumann N F, Samuel W M, Belosevic M: 1998, Meningeal worm evokes a heterogenous immune response in elk. J Wildl Dis 34: 334–341.

Call J L, Pilcher J B, Freeman Jr. G L et al.: 1995, Serum-free culturing of adult schistosoma mansoni in dialysis bags for the production of excretory/secretory antigens. J Parasit 81: 742–746.

Dauphine T C: 1975, The disappearance of caribou reintroduced to Cape Brenton Highlands National Park. Can Field Nat 89: 299–310.

Dew T L, Bowman D D, Grieve R B: 1992, Parasite-specific immunoglobulin in the serum and cerebrospinal fluid of white-tailed deer (*Odocoileus virginianus*) and goats (*Capra hircus*) with experimentally induced parelaphostrongylosis. J Zoo Wildl Med 23: 281–287.

Duffy M S, Tanner C E, Burt M D B: 1993, Serodiagnosis of *Parelaphostrongylus tenuis* in white-tailed deer *Odocoileus virginianus*. In Proceedings of the International Union of Game Biologists XXI Congress, I. D. Thompson (ed.) Halifax, Nova Scotia, Canada. p. 92–95.

Eckroade R J, Zurhein G M, Foreyt W: 1970, Meningeal worm invasion of the brain of a naturally infected white-tailed deer. J Wildl Dis 6: 430–436.

Forrester S G, Lankester M W: 1997, Extracting protostrongylid nematode larvae from ungulate feces. J Wildl Dis 33: 511–516.

Gajadhar A A, Tessaro S V, Yates W D G: 1994, Diagnosis of Elaphostrongylus cervi infection in New Zealand red deer (*Cervus elaphus*) quarantined in Canada, and experimental determination of a new extended prepatent period. Can Vet J 35: 433–437.

Gajadhar A A, Tessaro S V: 1995, Susceptibility of mule deer (*Odocoileus hemionus*) and two species of North American molluscs to *Elaphostrongylus cervi* (Nematoda: Metastrongyloidea). J Parasitol 81: 593–596.

Gamble H R, Anderson W R, Graham C E, et al.: 1983, Diagnosis of swine trichinosis by enzyme-linked immunosorbent assay (ELISA) using an excretory-secretory antigen. Vet Parasit 13: 349–361.

Gilbert F F: 1973, *Parelaphostrongylus tenuis* (Dougherty) in Maine I: The parasite in white-tailed deer (*Odocoileus virginianus* Zimmermann). J Wildl Dis 9: 136–143.

Krogdahl D W, Thilsted J P, Olsen S K: 1987, Ataxia and hypermetria caused by *Parelaphostrongylus tenuis* infection in llamas. J Am Vet Med Assoc 190: 191–193.

Lankester M W, Fong D: 1989, Distribution of elaphostrongyline nematodes (Metastrongyloidea: Protostrongylidae) in cervidae and possible effects of moving Rangifer spp. into and within North America. Alces 25: 133–145.

Lankester M W, Hauta P L: 1989, *Parelaphostrongylus andersoni* (Nematoda: Protostrongylidae) in caribou (*Rangifer tarandus*) of northern and central Canada. Can J Zool 67: 1966–1975.

Lankester M W, Peterson W J: 1996, The possible importance of deer wintering yards in the transmission of *Parelaphostrongylus tenuis* to white-tailed deer and moose. J Wildl Dis 32: 31–38.

Lehtonen O-P, Viljanen M K: 1982, A binding function for curve-fitting in enzyme-linked immunosorbent assay (ELISA) and its use in estimating the amounts of total and high affinity antibodies. International Journal of Bio-Medical Computing 13: 471–479.

Mayhew I G, de Lahunta A, Georgi J R et al.: 1976, Naturally occurring cerebrospinal parelaphostrongylosis. Cornell Vet 66: 56–72.

Nettles V F, Prestwood A K, Nichols R G et al.: 1977, Meningeal worm-induced neurological disease in black-tailed deer. J Wildl Dis 13: 137–143.

Neumann N F, Pon W S, Nowicki A et al.: 1994, Antigens of adults and third-stage larvae of the meningeal worm, *Parelaphostrongylus tenuis* (Nematoda, Metastrongyloidea). J Vet Diag Invest 6: 222–229.

Platt T R: 1984, Evolution of Elaphostrongylinae (Nematoda: Metastrongyloidea: Protostrongylidae) parasites of cervids (Mammalia). Proceedings of Helminthological Society of Washington 51: 196–204.

Prestwood A K: 1970, Neurologic disease in a white-tailed deer massively infected with meningeal worm (*Pneumostrongyus tenuis*). J Wildl Dis 6: 84–86.

Pybus M J, Samuel W M, Welch D A, et al.: 1992, Mortality of fallow deer (Dama dama) experimentally-infected with meningeal worm, *Parelaphostrongylus tenuis*. J Wildl Dis 28: 95–101.

Pybus M J, Samuel W M: 1984, *Parelaphostrongylus andersoni* (Nematoda: protostrongylidae) and *P. odocoilei* in two cervid definitive hosts. J Parasitol 70: 507–515.

Rickard L G, Smith B B, Gentz E J, et al.: 1994, Experimentally induced meningeal worm (*Parelaphostrongylus tenuis*) infection in the llama (*Lama glama*): Clinical evaluation and implications for parasite translocation. J Zoo Wildl Med 25: 390–402.

Samuel W M, Pybus M J, Welch D A, Wilke C J: 1992, Elk as a potential host for meningeal worm: implications for translocation. J Wildl Manage 56: 629–639.

Slomke A M, Lankester M W, Peterson W J: 1995, Infrapopulation dynamics of *Parelaphostrongylus tenuis* in white-tailed deer. J Wildl Dis 31:125–35.

Trainer D O: 1973, Caribou mortality due to the meningeal worm (*Parelaphostrongylus tenuis*) J Wildl Dis 9: 376–378.

Tyler G V, Hibler C P, Prestwood A K: 1980, Experimental infection of mule deer with *Parelaphostrongylus tenuis*. J Wildl Dis 16: 533–540.

Watson T G: 1984, Tissue worm in red deer. Symptoms and control. AgLink Farm Production and Practice 249 (1st revision), Media Services, Ministry of Agriculture and Food, Wellington, New Zealand, 2 pp.

Wild D: 1994, *The Immunoassay Handbook*. Stockton Press, N.Y., USA. p 83.

Welch D A, Pybus M J, Samuel W M et al.: 1991, Reliability of fecal examination for detecting infections of meningeal worm in elk. Wildl Soc Bull 19: 326–331.

Woolf A, Mason C A, Kradel D: 1977, Prevalence and effects of *Parelaphostrongylus tenuis* in a captive wapiti population. J Wildl Dis 13: 149–154.

Yamini B, Baker J C, Stromberg P C, Gardiner C H: 1997, Cerebrospinal nematodiasis and vertebral chondrodysplasia in a calf. J Vet Diagn Invest 9: 451–454.

What is claimed is:

1. A method of identifying common adult or larval Protostrongylidae antigens, comprising:
   (a) isolating proteins from adult or larval excretory-secretory (ES) products obtained from at least one member of the Protostrongylidae family; and
   (b) determining which ES protein products isolated in step (a) react with anti-Protostrongylidae antibodies obtained from two or more members of the Protostrongylidae family, thereby identifying antigens that are common to various members of the Protostrongylidae family.

2. A method of isolating one or more *P. tenuis*-specific antigens, comprising:
   (a) purifying proteins from the excretory-secretory products (ES) of *P. tenuis;* and
   (b) determining ES purified proteins that react with anti-*P. tenuis* antibodies, thereby isolating one or more *P. tenuis*-specific antigens.

* * * * *